(12) United States Patent
Basheer et al.

(10) Patent No.: US 10,689,607 B2
(45) Date of Patent: Jun. 23, 2020

(54) ENZYMATIC TRANSESTERIFICATION/ESTERIFICATION PROCESSES EMPLOYING LIPASES IMMOBILIZED ON HYDROPHOBIC RESINS IN THE PRESENCE OF WATER SOLUTIONS

(71) Applicant: Trans Bio-Diesel Ltd., Shfaram (IL)

(72) Inventors: Sobhi Basheer, Sakhnine (IL); Maisa Haj, Shfaram (IL); Usama Mohsen, Ibleen (IL); Doaa Shehadeh, Nazareth (IL); Ahmad Hindawi, Shfar-Am (IL); Emad Masoud, Arara (IL); Ahmad Egbarieh, Maeleh Eron (IL); Ramez Masri, Nahef (IL)

(73) Assignee: Trans Bio-Diesel Ltd., Shfaram (IL)

( * ) Notice: Subject to any disclaimer, the term of this patent is extended or adjusted under 35 U.S.C. 154(b) by 0 days.

(21) Appl. No.: 15/984,796

(22) Filed: May 21, 2018

(65) Prior Publication Data

US 2019/0002808 A1    Jan. 3, 2019

Related U.S. Application Data

(63) Continuation of application No. 13/597,304, filed on Aug. 29, 2012, now Pat. No. 10,000,731, which is a continuation-in-part of application No. PCT/IL2011/000699, filed on Aug. 31, 2011, which is a continuation-in-part of application No. PCT/IL2011/000121, filed on Feb. 2, 2011.

(60) Provisional application No. 61/309,122, filed on Mar. 1, 2010.

(51) Int. Cl.
| | |
|---|---|
| C12P 7/64 | (2006.01) |
| C12P 7/40 | (2006.01) |
| C12N 11/08 | (2020.01) |
| C12N 9/20 | (2006.01) |
| C12M 1/40 | (2006.01) |
| C12M 1/00 | (2006.01) |
| C12P 7/62 | (2006.01) |

(52) U.S. Cl.
CPC ............ *C12M 21/18* (2013.01); *C12M 23/58* (2013.01); *C12P 7/62* (2013.01); *C12P 7/649* (2013.01); *Y02E 50/13* (2013.01)

(58) Field of Classification Search
CPC ........ C12P 7/64; C12N 9/2417; C12M 21/18; C12Y 301/01003
USPC .............................. 435/134, 198, 280, 289.1
See application file for complete search history.

(56) References Cited

U.S. PATENT DOCUMENTS

| | | | |
|---|---|---|---|
| 7,238,504 B2 | 7/2007 | Sato et al. | |
| 7,790,429 B2 | 9/2010 | Basheer et al. | |
| 7,799,544 B2 | 9/2010 | Schorken et al. | |
| 7,906,305 B2 | 3/2011 | Sato et al. | |
| 8,252,560 B2 | 8/2012 | Saito et al. | |
| 2003/0068790 A1 | 4/2003 | Van Gemert et al. | |
| 2005/0233426 A1 | 10/2005 | Schoerken et al. | |
| 2006/0286266 A1 | 12/2006 | Saebo et al. | |
| 2009/0133322 A1 | 5/2009 | Basheer et al. | |

FOREIGN PATENT DOCUMENTS

| | | |
|---|---|---|
| CN | 101284999 A | 10/2008 |
| EP | 1582594 A2 | 10/2005 |
| EP | 2050823 A1 | 4/2009 |
| JP | H10-004992 A | 1/1998 |
| JP | 2008527154 A | 7/2008 |
| JP | 2008545407 A | 12/2008 |
| WO | 2008/084470 A2 | 7/2008 |
| WO | 2008/139455 A2 | 11/2008 |
| WO | 2009/069116 A2 | 6/2009 |
| WO | 2011/107977 A1 | 9/2011 |

OTHER PUBLICATIONS

Japanese App No. 2014-527808, Office Action, dated Oct. 15, 2015.
Yuecel, et al., Biomass and Bioenergy, Lipase Immobilization and Production of Fatty Acid Methyl Esters from Canola Oil using Immobilized Lipase, vol. 35, pp. 1496-1501, dated Feb. 23, 2011.
Severac et al, Enzyme and Microbial Technology, Selection of CalB Immobilization Method to be Used in Continuous Oil Transesterification: Analysis of the Economical Impact, vol. 48(1), pp. 61-70, dated Jan. 5, 2011.
Adamczak et al. Eur. J. Lipid Sci. 2009, 111, pp. 800-813.
M.L. Foresti, et al., "Interfacial activation and bioimprinting of Candida rugosa lipase immobilized on polypropylene: effect on the enzymatic activity in solvent-free ethyl oleate synthesis", ScienceDirect, vol. 36, Issues 2-3, Feb. 2005, pp. 338-349
Hossein Noureddini et al., "Immobilized Pseudornonas cepacia lipase for biodiesel fuel production from soybean oil", Chemical and Biomolecular Engineering Research and Publications, May 1, 2004, 15 pages.
Juxi et al, Study on geotrichum candidum lipase immobilization and its catalysis of synthesis of biodiesel from Cornus wilsoniana oil, Cereals and Oils Processing, No. 4: 31-35 (2010).
Ying, "Study on immobilization of lipase and its application", China Masters' Thesis Full-Text Database, www.cnki.net (2009).
Shaw et al., Biotechnology and Bioengineering 35:132-137 (1990). "Lipolytic Activities of a Lipase Immobilized on Six Selected Supporting Materials."

(Continued)

*Primary Examiner* — Robert B Mondesi
*Assistant Examiner* — Mohammad Y Meah
(74) *Attorney, Agent, or Firm* — Banner & Witcoff, Ltd.

(57) ABSTRACT

Disclosed are an enzymatic batchwise or continuous process for the production of fatty acid alkyl esters for use in the biofuels, food and detergent industries and a system therefor. The process utilizes enzymes immobilized on a hydrophobic resin mixed with a fatty acid source and an alcohol or alcohol donor in the presence of an alkaline or mild alkaline aqueous buffer, or in the presence of water or aqueous solution. The production process for fatty acid alkyl esters is carried out by transesterification or esterification simultaneously or sequentially. The biocatalyst activity is maintained with no significant activity losses in multiple uses and also avoids the accumulation of glycerol and water by-products or other hydrophilic compounds on the biocatalyst.

12 Claims, 18 Drawing Sheets

(56) References Cited

OTHER PUBLICATIONS

Mackenzie et al., Enzyme and Microbial Technology, 27:302-311 (2000). "Production of high-oleic acid tallow fractions using lipase-catalyzed direct interesterification, using both batch and continuous processing."
Foresti et al., Enzyme and Microbial Technology, 41(1-2):62-70 (2007). "Multiple effects of water on solvent-free enzymatic esterifications."
Chen et al., World Journal of Microbiology and Biotechnology, 24(10):2097-2102 (2008). "Effect of several factors on soluble lipase-mediated biodiesel preparation in the biphasic aqueous-oil systems."
Kim et al., Biotechnology and Bioprocess Engineering, 12:441-445 (1007). "Lipase catalyzed transesterification of soybean oil using ethyl acetate, an alternative acyl acceptor".
Salis et al., Journal of Molecular Catalysis, 57:262-269 (2009). "Role of the support surface of the loading and the activity of Pseudomonas fluorescens lipase used for biodiesel synthesis."
Hernandez et al., Enzyme and Microbial Technology, 49:72-28 (2011). "Simple and efficient immobilization of lipase B from Candida antarctica on porous styrene-divinylbenzene beads."

US 10,689,607 B2

ENZYMATIC TRANSESTERIFICATION/ESTERIFICATION PROCESSES EMPLOYING LIPASES IMMOBILIZED ON HYDROPHOBIC RESINS IN THE PRESENCE OF WATER SOLUTIONS

CROSS-REFERENCE TO RELATED APPLICATIONS

This application is a Continuation of application Ser. No. 13/597,304 filed on Aug. 29, 2012, U.S. Pat. No. 10,000,731, which is a Continuation-in-part application of International Application No. PCT/IL2011/000121 filed on Feb. 2, 2011, which claims benefit under 35 U.S.C. 119(e) of U.S. Provisional Application No. 61/309,122 filed on Mar. 1, 2010; and which is a Continuation-in-part application of International Application No. PCT/IL2011/000699 filed on Aug. 31, 2011, the contents of which are herein incorporated by reference in their entirety.

FIELD OF THE INVENTION

Disclosed is an enzymatic process for the production of fatty acid alkyl esters for use in the biofuels, food and detergent industries. In this process a fatty acid source and an alcohol or alcohol donor are reacted in the presence of enzymes immobilized on a hydrophobic resin, in the presence of an alkaline aqueous buffer or water. The disclosed process can be operated either batchwise or continuously using a continuous stirred-tank or packed-bed column reactors.

BACKGROUND OF THE INVENTION

Immobilization of enzymes has been described by a vast number of techniques basically aiming at reducing the cost contribution of enzymes in the overall enzymatic process; facilitating recovery of enzymes from the products; and enabling continuous operation of the process.

Immobilization techniques are in general divided according to the following:
1. Physical adsorption of enzymes to solid supports, such as silica and insoluble polymers.
2. Adsorption on ion-exchange resins.
3. Covalent binding of enzymes to a solid support material, such as epoxidated inorganic or polymeric supports.
4. Entrapment of enzymes in a growing polymer.
5. Confinement of enzymes in a membrane reactor or in semi-permeable gels.
6. Cross-linking enzyme crystals (CLECS's) or aggregates (CLEAS's).

All the aforementioned enzyme immobilization procedures are comprised of the following steps:
1. Dissolving the enzyme in an appropriate buffer system with respect to pH, temperature, type of buffer salts and ionic strength.
2. Adding the solid support into the enzyme solution and mixing for some time till enzyme molecules are immobilized on the solid support.
3. Filtering off the solid support which contains the immobilized enzyme.
4. Washing the support with an appropriate buffer to remove loosely bound enzyme molecules and then drying the solid support.

Interfacial enzymes, mostly lipases, have been immobilized following the aforementioned techniques. These offered immobilized enzyme preparations possessing low synthetic activity and/or short operational half-life time. In an attempt to increase the synthetic activity and stability of immobilized lipases and other interfacial enzymes different activation methods have been applied. These methods include:
1. Binding the surface functional groups of enzymes with hydrophobic residues such as fatty acids or polyethylene glycol.
2. Coating the surface of enzymes with surfactants, such as polyol fatty acid esters.
3. Contacting enzymes with hydrophobic supports, typically polypropylene, which have been pretreated with hydrophilic solvents, such as ethanol or iso-propanol.

None of the above mentioned methods yielded satisfactory results with respect to stabilization and cost-effectiveness of immobilized interfacial enzymes, in order to carry out enzymatic reverse conversions at industrial quantities. Also, it has been reported that most enzymes, when immobilized according to the aforementioned procedures, either lose a significant portion of their synthetic activity or they do not exhibit their full activity performance due to certain constraints imposed by the immobilization procedure, or because of the presence of certain enzyme inhibitors in the reaction medium.

Another major drawback of lipases and phospholipases is their low tolerance towards hydrophilic substrates, in particular short-chain alcohols and short-chain fatty acids (below C4). It has been observed in many research studies that short-chain alcohols and short-chain fatty acids, such as methanol and acetic acid, respectively, are responsible for detaching essential water molecules from the quaternary structure of those enzymes, leading to their denaturation and consequently loss of their catalytic activity. This drawback has prohibited the application of lipases for production of commercial quantities of fatty acids methyl esters "biodiesel" using oil triglycerides and methanol as substrates.

An additional drawback of using immobilized lipases for transesterification/esterification of a fatty acid source with a free alcohol is the accumulation of the formed glycerol and water by-products on the biocatalyst and therefore prohibiting the substrates from free access to the active site of the immobilized enzyme. Such biocatalysts generally lose their catalytic performance after a few cycles when the same batch of biocatalyst is used.

The present inventors have developed special immobilized enzyme preparations, exhibiting good stability over many production cycles, persisting activity. Examples of such enzyme preparations are disclosed, inter alia, in WO/2008/084470, WO/2008/139455 and WO2009/069116.

Conditions under which the catalytic reaction is carried out, may adversely affect the stability and efficiency of immobilized enzyme preparations. It is important to have enzyme preparations which retain stability and activity under the reaction conditions.

These and other objects of the invention will become apparent as the description proceeds.

SUMMARY OF THE INVENTION

In one embodiment, the invention relates to a process for the transesterification/esterification of a fatty acid source with an alcohol, to form fatty acid alkyl esters, comprising reacting a fatty acid source and an alcohol or an alcohol donor in the presence of an immobilized lipase preparation, wherein the immobilized lipase preparation comprises at least one lipase immobilized on a hydrophobic porous support and the reaction medium contains an aqueous alkaline buffer solution.

In all aspects of this embodiment, the said aqueous alkaline buffer solution may be a mild aqueous alkaline buffer solution. The said aqueous alkaline buffer solution may be contained in the reaction mixture at a quantity of up to 99% wt. of the fatty acid source, for example, up to 90%, 80%, 70%, 60%, 50%, 40%, 30%, 25%, 20%, 15%, 12%, 10%, 8%, 5%, 4%, 3%, 2%, and 1%. Alternatively, the said aqueous alkaline buffer solution may be contained in the reaction mixture at a quantity of more than 1% wt. of the fatty acid source, more than 2%, 3%, 4%, 5%, 6%, 8%, 10%, 12%, 15%, 20%, 25%, 30%, 40%, 50%, 60%, 70%, 80%, 90%, and up to 99%. The aqueous buffer solution may have a pH from 7 to about 11, for example any one of 7-8.5, 7-9, 7-9.5, 7-10 and 7-11. In the process of the invention, the pKa of the supplemented mild alkaline reagent comprising of the buffer solution may be higher than or equal to the pKa of free acids present in the fatty acid source.

In another embodiment the invention relates to a process for the transesterification/esterification of a fatty acid source with an alcohol, to form fatty acid alkyl esters, comprising reacting a fatty acid source and an alcohol in the presence of an immobilized lipase preparation, wherein the immobilized lipase preparation comprises at least one lipase immobilized on a hydrophobic porous support and the reaction medium contains water. The water is in the form of distilled water or water containing various dissolved salts, with a pH of from 3 to 11. In all aspects of this embodiment, the reaction medium may contain the water or water solution at a quantity of up to 99% wt. of the fatty acid source, for example, up to 90%, 80%, 70%, 60%, 50%, 40%, 30%, 25%, 20%, 15%, 12%, 10%, 8%, 5%, 4%, 3%, 2%, and 1%. Alternatively, the water or water solution may be contained in the reaction mixture at a quantity of more than 1% wt, of the fatty acid source, more than 2%, 3%, 4%, 5%, 6%, 8%, 10%, 12%, 15%, 20%, 25%, 30%, 40%, 50%, 60%, 70%, 80%, 90%, and up to 99%.

In all embodiments and aspects of the invention, the alcohol may be a short-chain alcohol, for example C1-C6 alkyl alcohol, more specifically C1-C4 alkyl alcohol, particularly methanol or ethanol. Where said alcohol is methanol said resulting fatty acid esters are fatty acid methyl esters (FAME—Biodiesel). The alcohol may also be a medium-chain fatty alcohol (C6-C10) or long-chain fatty alcohols (C12-C22). The alcohol donor may be a mono-alkyl ester or a di-alkyl carbonate, such as di-methyl carbonate or diethyl carbonate.

In all embodiments and aspects of the invention, said immobilized lipase is capable of catalyzing the esterification of free fatty acids to yield fatty acid alkyl esters and water as by-product, and the transesterification of triglycerides, partial glycerides, wax esters, and phospholipids to yield fatty acid alkyl esters and glycerol, and long-chain fatty alcohols and glycerophospholipids as by-products, respectively.

In all embodiments and aspects of the invention related to the use of an alkaline buffer or alkaline solution, the amount of said alkaline buffer or solution in the reaction medium is more than 0.001% wt. of the fatty acid source.

In all embodiments and aspects of the invention, said at least one lipase may be a lipase derived from any one *Rhizomucor miehei, Pseudomonas* sp., *Rhizopus niveus, Mucor javanicus, Rhizopus oryzae, Aspergillus niger, Penicillium camembertii, Alcaligenes* sp., *Acromobacter* sp., *Burkholderia* sp., *Thermomyces lanuginosus, Chromobacterium viscosum, Candida antarctica* B, *Candida rugosa, Candida antarctica* A, papaya seeds and pancreatin. The lipase preparation may comprise at least two lipases which may be each separately immobilized on a hydrophobic support or co-immobilized on the same hydrophobic support. The said lipases are capable of simultaneously or consecutively catalyzing the esterification of free fatty acids to yield fatty acid alkyl esters and water as by-product, and the transesterification of triglycerides and partial glycerides to yield fatty acid alkyl esters and glycerol as by-product, and/or transesterification of phospholipids to yield fatty acid alkyl esters and lysophospholipids and glycerophospholipids as by-products.

In all embodiments and aspects of the invention, said support may be any one of hydrophobic aliphatic polymer-based support and hydrophobic aromatic polymer-based support. The said hydrophobic polymer support may be comprised of linear or branched organic chains. The said support may comprise macroreticular organic polymer or co-polymer chains. The said support may be porous or non-porous inorganic support, which may be hydrophobic or is coated with hydrophobic organic material. The said organic material may be a linear, branched, or functionalized hydrophobic organic chain.

In all embodiments and aspects of the invention where an alkaline buffer solution is used, said aqueous alkaline buffer solution may be a solution of an inorganic alkaline salt or an organic base. The said alkaline buffer solution may be a solution of any one of an alkaline metal hydroxide, carbonate, bicarbonate, phosphate, sulfate, acetate and citrate, fatty acid salts, a primary, secondary and tertiary amine, and any mixture thereof. In specific embodiments, the said alkaline buffer solution may be a solution of a weak base selected from sodium or potassium bicarbonates and carbonates. In some specific embodiments of the process of the invention, the said alkaline buffer solution may be added to said fatty acid source in a pre-mixing stage or directly to the reaction medium.

In all embodiments and aspects of the invention where an alkaline buffer solution is used, the content of said alkaline buffer solution in the transesterification/esterification reaction medium may be in an amount of more than 0.001% wt. of the oil feedstock, for example 1-30% wt., 1-20% wt., 1-10% wt., 1-5% wt. or 1-2% wt. of the oil feedstock, or amounts of more than 5% wt. of the oil feedstock, for example more than 6%, 7%, 8%, 10%, 12%, 15%, 20%, 30%, 40% and 50% wt. of the oil feedstock.

In some embodiments of the invention, the fatty acid source may be first mixed with the alkaline buffer solution or with the water or water solution, and the mixture may be then treated with said immobilized lipase preparation, followed by adding said alcohol and allowing the reaction to proceed under suitable conditions until said fatty acid source is converted to fatty acid esters.

In all embodiments and aspects of the invention said fatty acid source may be any one of plant oil, animal fat, algae oil, fish oil, waste oil and any mixtures thereof. The said fatty acid source may comprise free fatty acids, mono-, di- or tri-glycerides, their mixtures at any ratio, in the absence or presence of other minor fatty acid derivatives such as phospholipids, wax esters and sterol esters. The fatty acid source may be unrefined, refined, bleached, deodorized or any of their combinations.

In all embodiments and aspects of the invention, the reaction may be carried out at a temperature between 10° C. and 100° C., specifically between 25-30° C.

In all embodiments and aspects of the invention, the said fatty acid source may be pre-mixed with said alcohol or alcohol donor and with said water or buffer solution in a pre-reaction preparation vessel to form an emulsion which may then be fed together with said immobilized lipase preparation into a transesterification/esterification reaction vessel.

In all embodiments and aspects of the invention, said immobilized lipase may be used in packed-bed column reactors operating in batch or continuous modes.

According to another aspect of the invention there is provided a system for the transesterification/esterification of a fatty acid with an alcohol, to form fatty acid alkyl esters, comprising:
  a reaction vessel configured for reacting a reaction medium including a fatty acid and at least one of an alcohol and an alcohol donor in the presence of an immobilized lipase preparation, wherein the immobilized lipase preparation comprises at least one lipase immobilized on a hydrophobic porous support and the reaction medium contains at least one of an aqueous alkaline buffer solution and water.

The system may comprise one or more of the following features, in any desired combination or permutation:
A. The reaction vessel can comprise the immobilized lipase preparation, at least during operation of said system for the production of said fatty acid alkyl esters.
B. Additionally or alternatively to feature A, the reaction vessel can comprise the fatty acid and the at least one of an alcohol and an alcohol donor, at least during operation of said system for the production of said fatty acid alkyl esters.
C. Additionally or alternatively to features A or B, said reaction medium comprises a mixture, said system further comprising a pre-reaction vessel in selective fluid communication with said reaction vessel, said pre-reaction vessel being configured for premixing at least the fatty acid and the at least one of an alcohol and an alcohol donor to form said mixture, and for selectively delivering said mixture to said reaction vessel at least during operation of said system for the production of said fatty acid alkyl esters. The system can optionally further comprise a fatty acid source in selective fluid communication with said pre-reaction vessel and configured for selectively delivering the fatty acid to said pre-reaction vessel at least during said operation of said system, and an alcohol source in selective fluid communication with said pre-reaction vessel and configured for selectively delivering the at least one of an alcohol and an alcohol donor to said pre-reaction vessel at least during said operation of said system. The system can optionally further comprise a buffer source in selective fluid communication with said pre-reaction vessel and configured for selectively delivering the at least one of an aqueous alkaline buffer solution and water to said pre-reaction vessel to be included in said mixture at least during said operation of said system.
D. Additionally or alternatively to features A to C, the system can be configured for selectively delivering one or more of the fatty acid and/or the at least one of an alcohol and an alcohol donor and/or the at least one of an aqueous alkaline buffer solution and water to said pre-reaction vessel each in either a continuous manner or in discrete batches, at least during said operation of said system.
E. Additionally or alternatively to features A to D, the pre-reaction vessel can be configured for selectively delivering said mixture to said reaction vessel in a continuous manner and/or in discrete batches at least during said operation of said system.
F. Additionally or alternatively to features A to E, the system can be configured for selectively and directly delivering to said reaction vessel at least one of the fatty acid; the at least one of an alcohol and an alcohol donor; and the at least one of an aqueous alkaline buffer solution and water.
G. Additionally or alternatively to features A to F, the reaction vessel can comprise a thermal regulation system configured for maintain the reaction medium in said reaction vessel within a selected temperature range.
H. Additionally or alternatively to features A to G, the system can optionally further comprise a retaining arrangement configured for retaining the immobilized lipase preparation within said reaction vessel at least during operation of said system.
I. Additionally or alternatively to features A to H, the system further comprises a product separation vessel in selective fluid communication with said reaction vessel, said system being configured for selectively delivering a reaction mixture including reaction products from said reaction vessel to said product separation vessel, and wherein said product separation vessel is configured for selectively separating a yield of the fatty acid alkyl esters from the reaction mixture delivered thereto. For example, the product separation vessel can be one of a centrifuge and gravity separation system.
J. Additionally or alternatively to features A to I, the reaction vessel is configured for selectively delivering said reaction mixture to said product separation vessel in a continuous manner and/or in discrete batches at least during said operation of said system.
K. Additionally or alternatively to features I to J, the system is configured for selectively delivering said yield of fatty acid alkyl esters from said product separation vessel. For example, the system is configured for selectively delivering said yield of fatty acid alkyl esters from said product separation vessel in a continuous manner and/or in discrete batches.
L. Additionally or alternatively to features A to K, the system is configured for increasing said yield of the fatty acid alkyl esters from the reaction mixture delivered to said product separation vessel. In one configuration of the system having this feature, the system is configured for selectively rerouting said yield of the fatty acid alkyl esters to said reaction vessel to further increase said yield of the fatty acid alkyl esters from the reaction mixture subsequently delivered to said product separation vessel. In another configuration of the system having this feature, the system is configured for selectively rerouting said yield of the fatty acid alkyl esters to an auxiliary reactor module, wherein said auxiliary reactor module comprises an auxiliary reactor vessel and an auxiliary product separation vessel, wherein said further increased yield of the fatty acid alkyl esters is selectively subsequently delivered via said auxiliary product separation vessel.

BRIEF DESCRIPTION OF THE FIGURES

In order to understand the invention and to see how it may be carried out in practice, embodiments will now be described, by way of non-limiting example only, with reference to the accompanying drawings, in which.

*Pseudomonas* sp. (PS) immobilized on Sepabeads SP70 (SB SP70) as a hydrophobic resin and on porous silica (Sil.) as a hydrophilic resin.

Abbreviations: Conv.—conversion; Cyc.—Cycle

Figure 2:
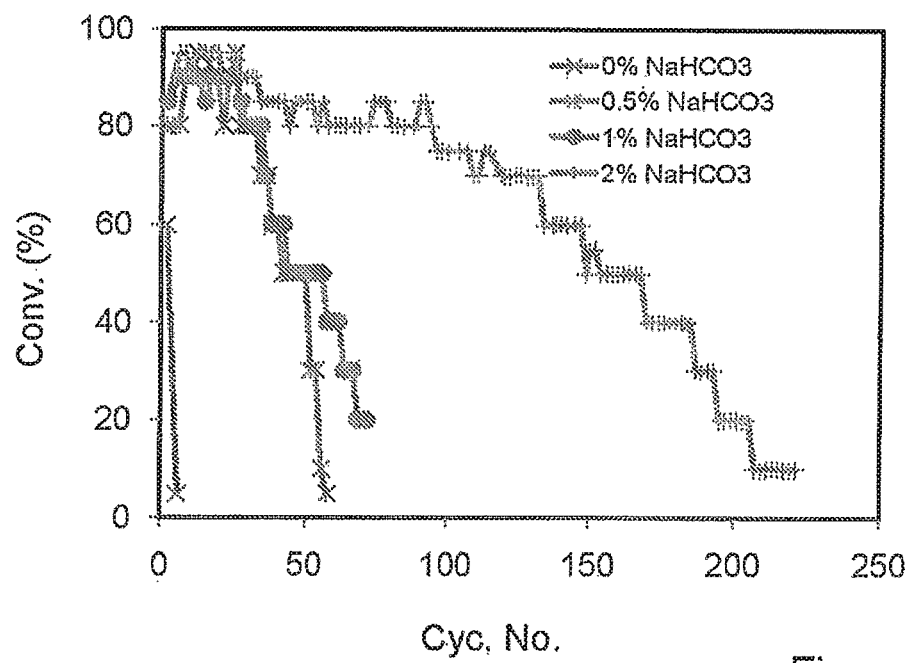

FIG. 2: The conversion of soybean oil to biodiesel and glycerol after 6 hours of reaction at different levels of sodium bicarbonate solution of 0.1M using the same batch of biocatalyst in multiple batch experiments. Biocatalyst was lipase derived from *Thermomyces lanuginosus* immobilized on a hydrophobic and porous polystyrene-divinylbenzene-based resin.

Abbreviations: Conv.—conversion; Cyc.—cycle

Figure 3:
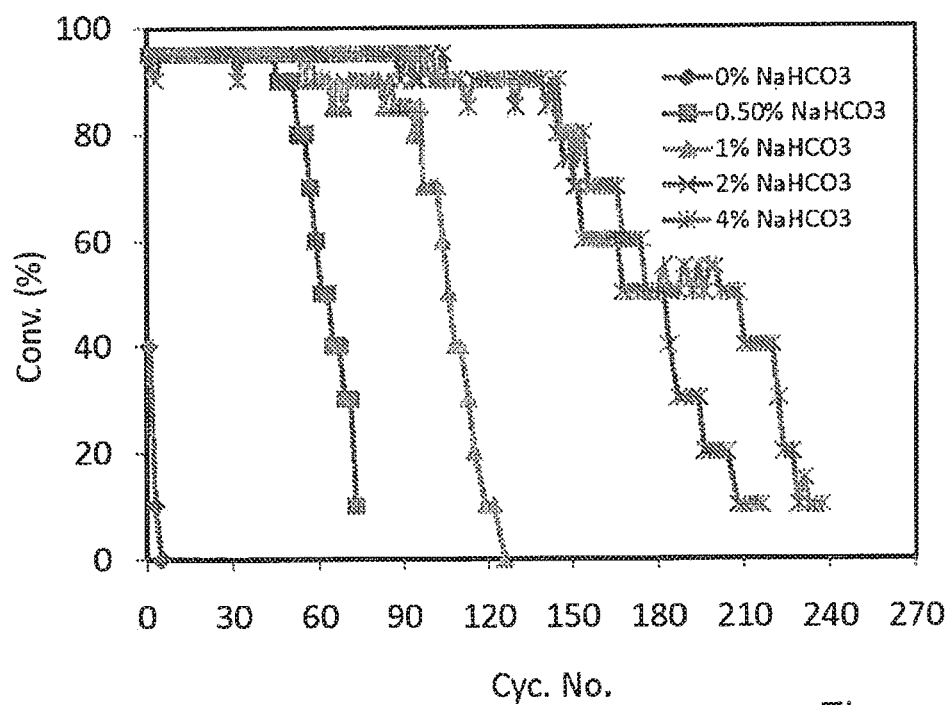

FIG. 3: The conversion of soybean oil to biodiesel and glycerol after 6 hours of reaction at different levels of sodium bicarbonate solution of 0.1M using the same batch of biocatalyst in multiple batch experiments. Biocatalyst was lipase derived from *Pseudomonas* sp. immobilized on a hydrophobic and porous polystyrene-divinylbenzene-based resin.

Abbreviations: Conv.—conversion; Cyc.—cycle

Figure 4:
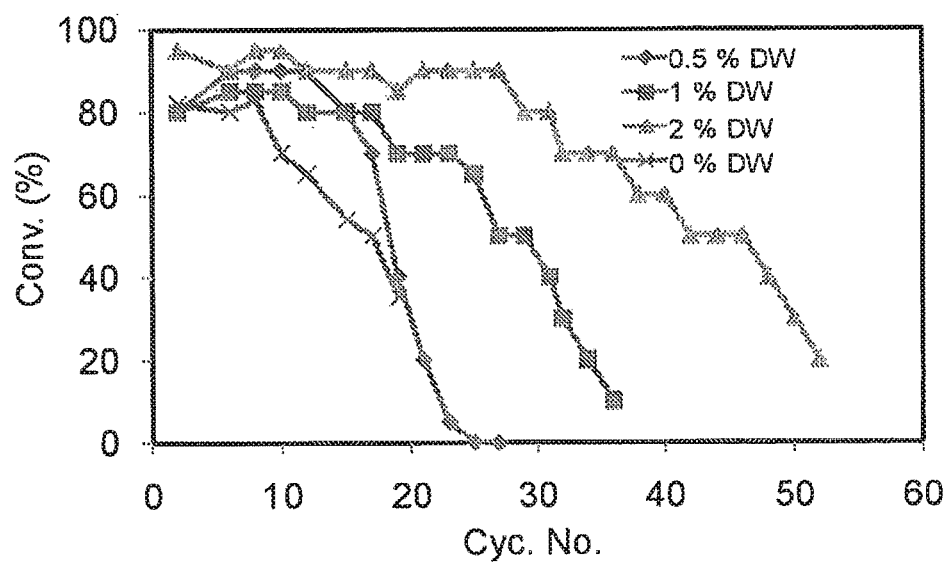

FIG. 4: The conversion of soybean oil to biodiesel and glycerol after 6 hours of reaction without water and at different levels of water using the same batch of biocatalyst in multiple batch experiments. Biocatalyst was lipase derived from *Thermomyces lanuginosus* immobilized on a hydrophobic and porous polystyrene-divinylbenzene-based resin.

Abbreviations: Conv.—conversion; Cyc.—cycle; DW—distilled water

Figure 5:
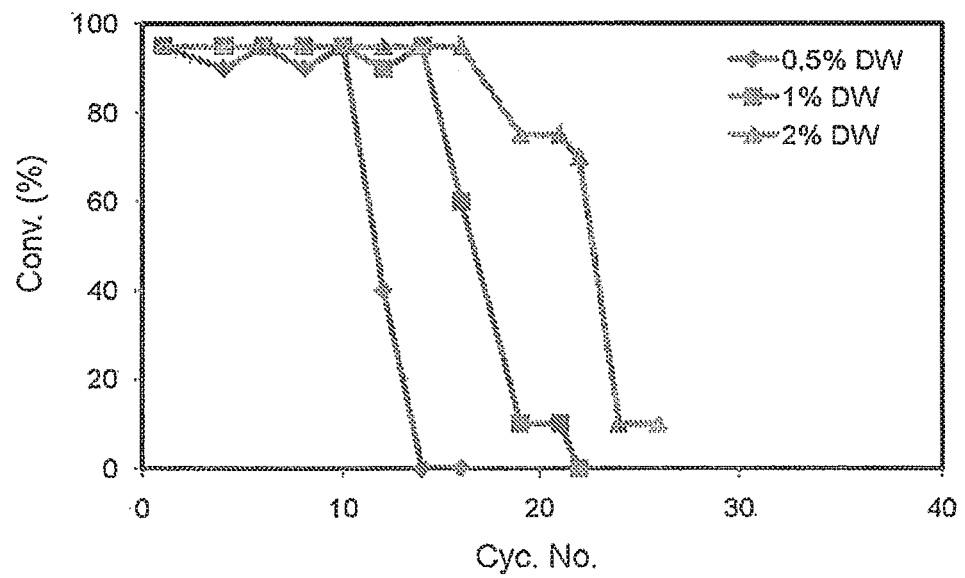

FIG. 5: The conversion of soybean oil to biodiesel and glycerol after 6 hours of reaction at different levels of water using the same batch of biocatalyst in multiple batch experiments. Biocatalyst was lipase derived from *Pseudomonas* sp. immobilized on a hydrophobic and porous polystyrene-divinylbenzene-based resin.

Abbreviations: Conv.—conversion; Cyc.—cycle; DW—distilled water

Figure 6:
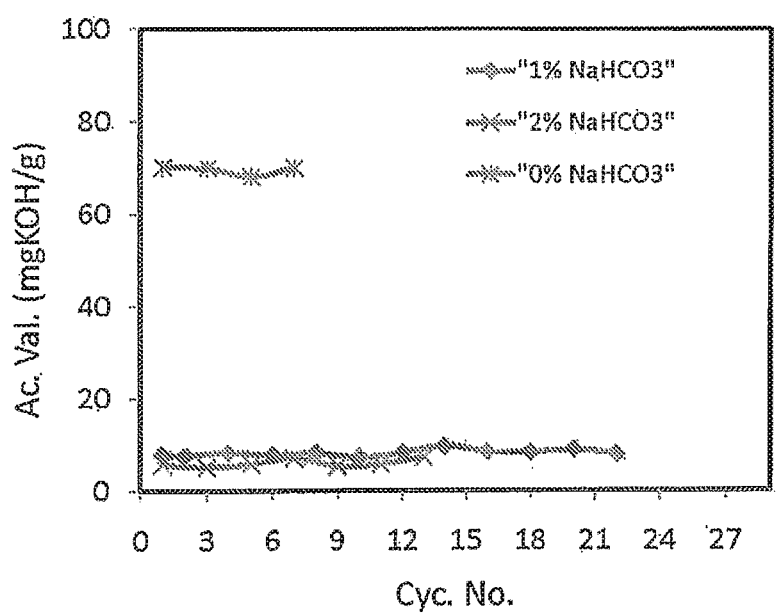

FIG. 6: The conversion of a mixture of FFA's and soybean oil to biodiesel, and glycerol and water by-products after 4 hours of esterification/transesterification at different levels of sodium bicarbonate solution of 0.1M using the same batch of biocatalyst in multiple batch experiments. Biocatalyst was lipase derived from *Pseudomonas* sp. immobilized on a hydrophobic and porous polystyrene-divinylbenzene-based resin.

Abbreviations: Conv.—conversion; Cyc.—cycle; DW—distilled water

Figure 7:
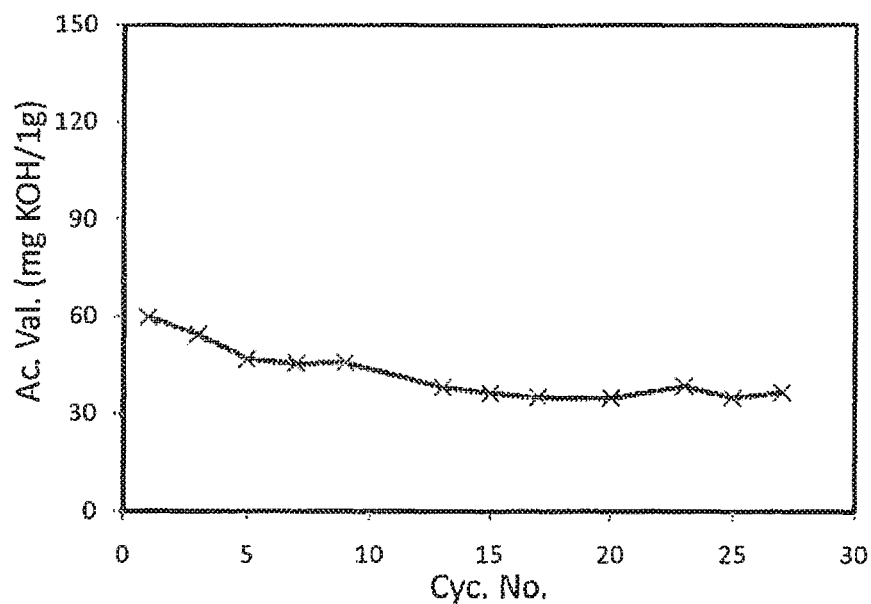

FIG. 7: The esterification of soybean oil hydrolysate to biodiesel and water after 4 hours of reaction in the presence of 2% sodium bicarbonate solution of 0.1M using the same batch of biocatalyst in multiple batch experiments. Biocatalyst was lipase derived from *Pseudomonas* sp. immobilized on a hydrophobic and porous polystyrene-divinylbenzene-based resin.

Abbreviations: Ac. Val.—acid value; Cyc.—cycle

Figure 8:
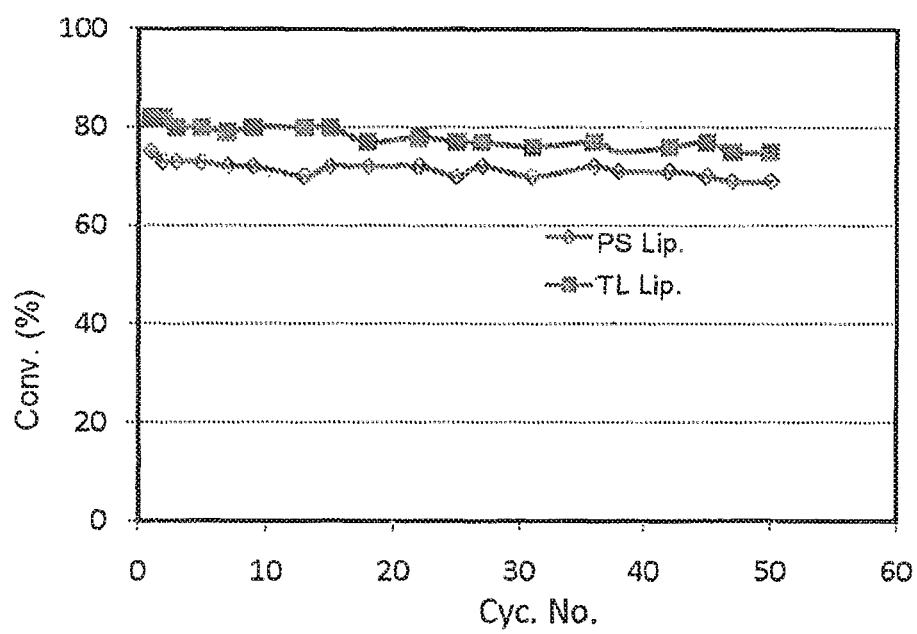

FIG. 8: The transesterification of fish oil with ethanol after 6 hours of reaction in the presence of 1% wt. of sodium bicarbonate solution of 0.1M using the same batch of biocatalyst in multiple batch experiments. The biocatalysts were lipases derived from *Thermomyces lanuginosus* (TL Lip.) and *Pseudomonas* sp. (PS Lip.) immobilized on Amberlite XAD 1600.

Abbreviations: Conv.—conversion; Cyc.—cycle

Figure 9:
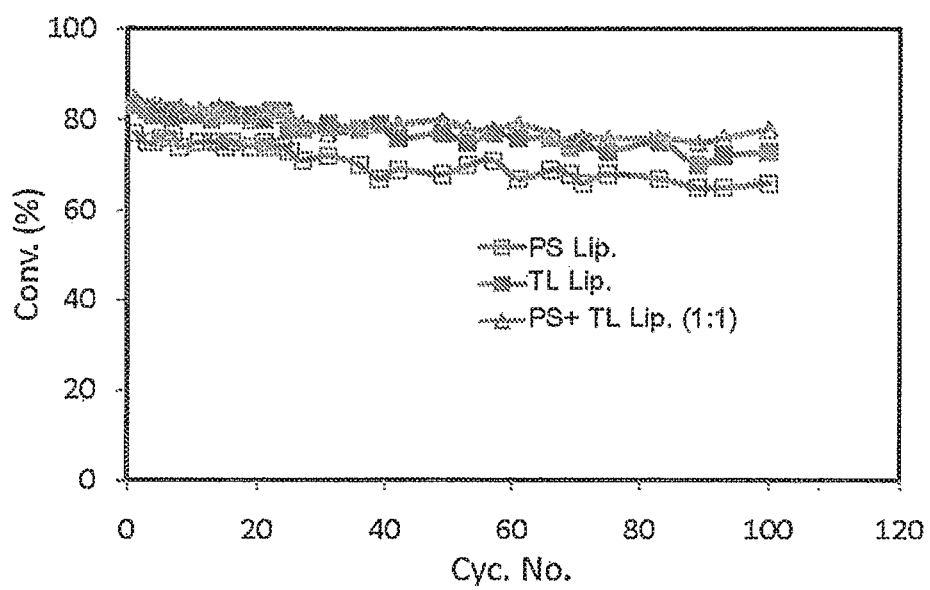

FIG. 9: The transesterification of Tallow fat with ethanol after 6 hours of reaction in the presence of 2% wt. of sodium bicarbonate solution of 0.1M using the same batch of biocatalyst in multiple batch experiments. The biocatalysts were *Thermomyces lanuginosus*, *Pseudomonas* sp. lipases (PS Lip.; TL Lip.) immobilized on Amberlite XAD 1600.

Abbreviations: Conv.—conversion; Cyc.—cycle

Figure 10:
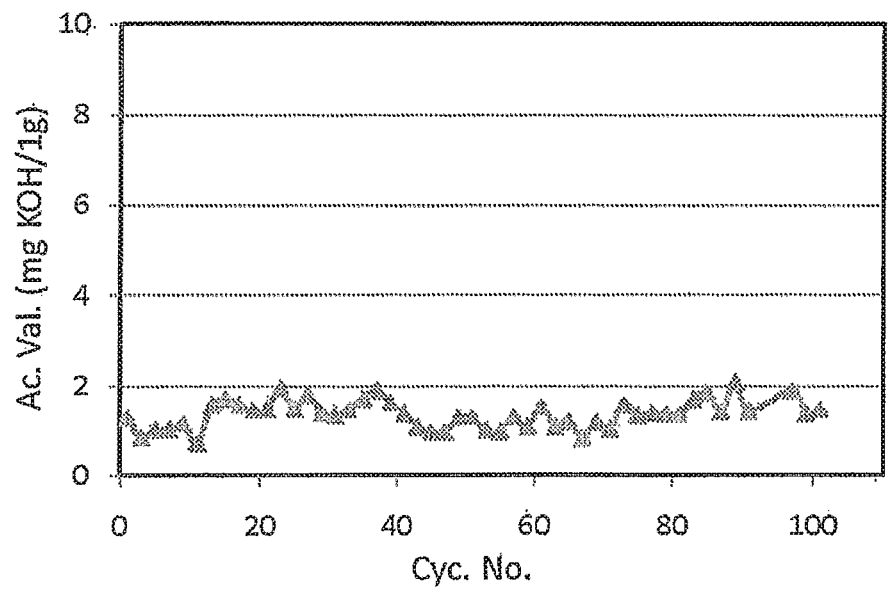

FIG. 10: The treatment of the transesterification/esterification reaction medium obtained after 4 hours containing FFA value of 7 mg KOH/1 g using *Pseudomonas* sp. or *Thermomyces lanuginosus* immobilized on hydrophobic porous resins with *Candida Antarctica* immobilized on a hydrophobic porous resin.

Abbreviations: Ac. Val.—acid value; Cyc.—cycle

Figure 11:
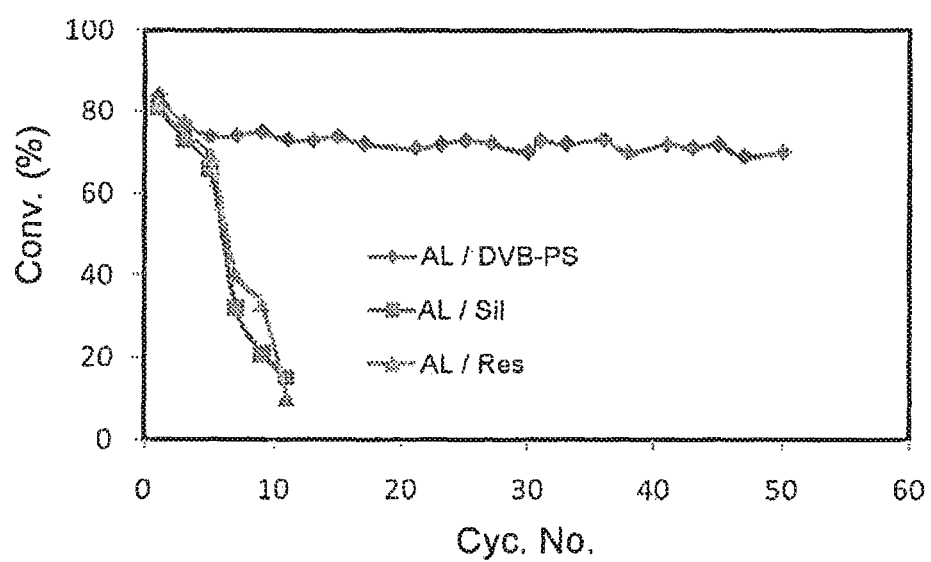

FIG. 11: The transesterification activity of lipase derived from *Alcaligenes* sp. (AL) immobilized on divinylbenzene/polystyrene (DVB-PS) as a hydrophobic resin, on a weak anion exchange hydrophilic resin (Res.), and on porous silica granulated (Sil) as a hydrophilic resin.

Abbreviations: Conv.—conversion; Cyc.—cycle

Figure 12:
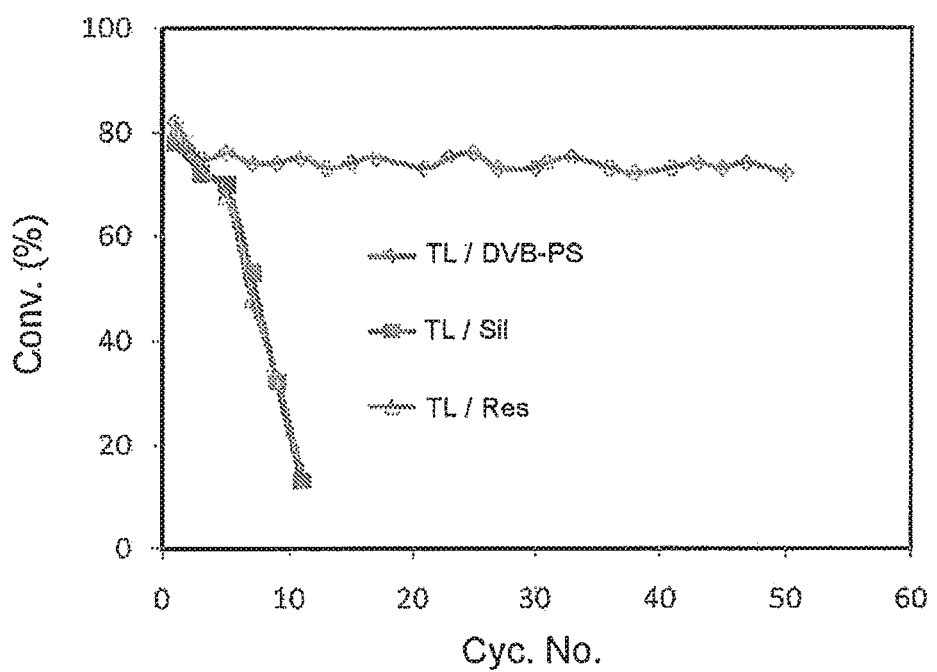

FIG. 12: The transesterification activity of *Thermomyces lanuginosus* (TL) lipase immobilized on divinylbenzene/polystyrene (DVB-PS) as a hydrophobic resin, on a weak anion exchange hydrophilic resin (Res.), and on porous silica granulated (Sil) as a hydrophilic resin.

Abbreviations: Conv.—conversion; Cyc.—cycle

Figure 13:
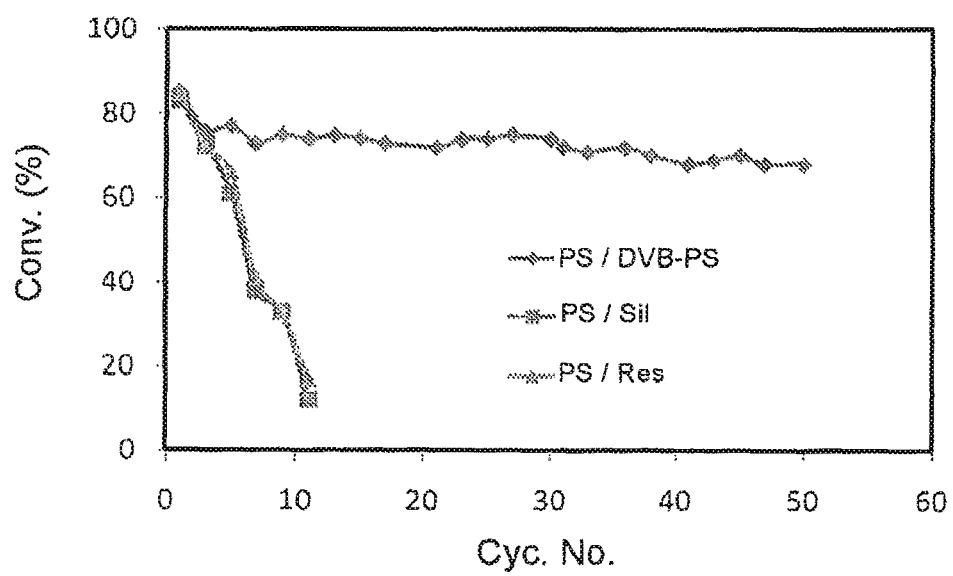

FIG. 13: The transesterification activity of *Pseudomonas* sp. (PS) lipase immobilized on divinylbenzene/polystyrene (DVB-PS) as a hydrophobic resin, on a weak anion exchange hydrophilic resin (Res), and on porous silica granulated (Sil) as a hydrophilic resin.

Abbreviations: Conv.—conversion; Cyc.—cycle

Figure 14:
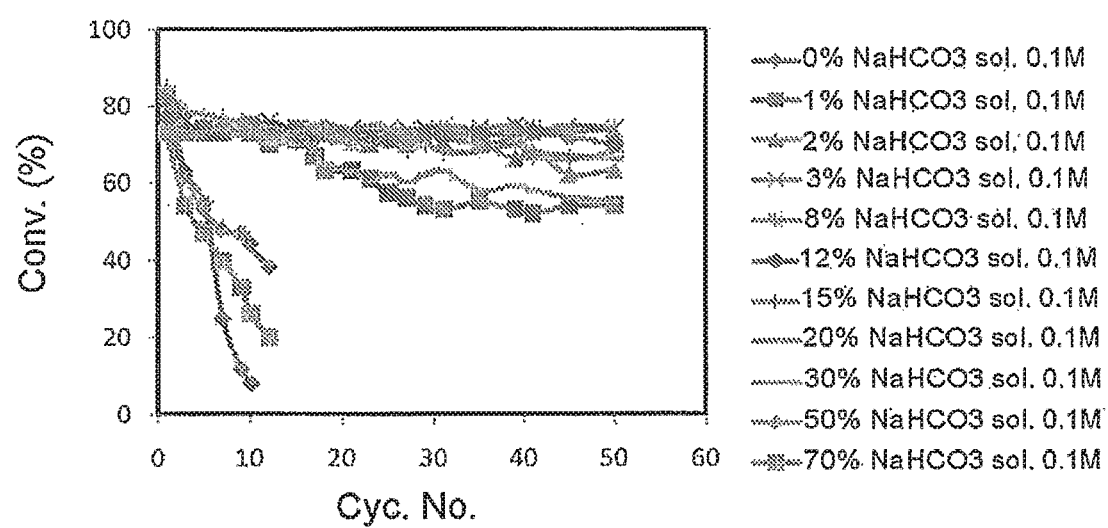

FIG. 14: The conversion of soybean oil to fatty acid methyl esters and glycerol after 6 hours of reaction using the same batch of biocatalyst (*Thermomyces lanuginosus* (TL) immobilized on a DVB-PS support) in multiple batch experiments, at different concentrations of sodium bicarbonate solution of 0.1M. Methanol was added to the reaction mixture in one step on molar basis ratio of 1:3 between oil and methanol.

Abbreviations: Conv.—conversion; Cyc.—cycle; Sol.—solution

Figure 15:
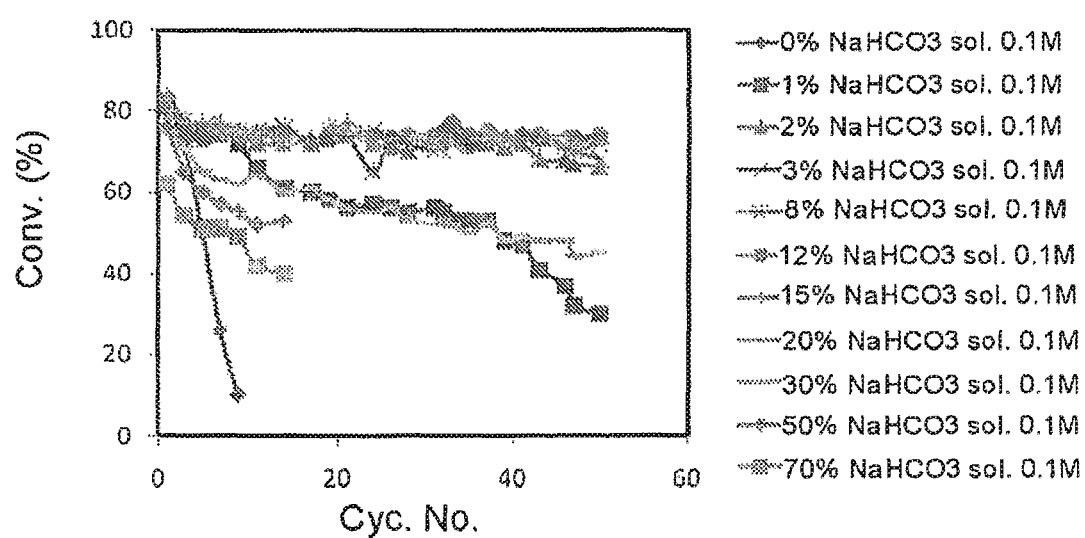

FIG. 15: The conversion of soybean oil to biodiesel and glycerol after 6 hours of reaction using the same batch of biocatalyst (*Pseudomonas* sp. (SP) immobilized on a DVB-PS support) in multiple batch experiments at different concentrations of sodium bicarbonate solution of 0.1M. Methanol was added to the reaction mixture in one step on molar basis ratio of 1:3 between oil and methanol.

Abbreviations: Conv.—conversion; Cyc.—cycle; Sol.—solution

Figure 16:
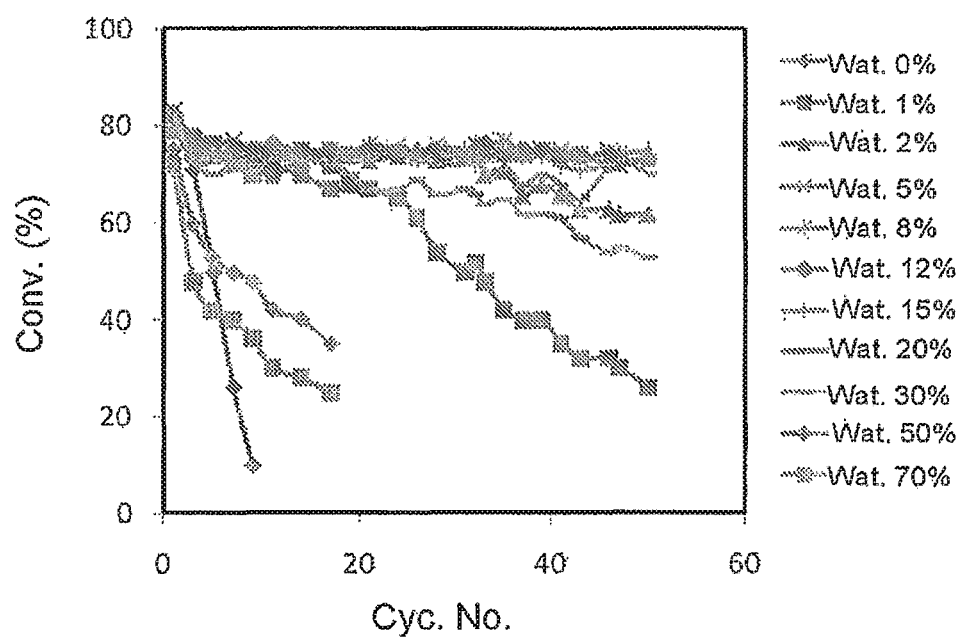

FIG. 16: The conversion of soybean oil to biodiesel and glycerol after 6 hours of reaction using the same batch of (*Thermomyces lanuginosus* (TL) immobilized on a DVB-PS support) in multiple batch experiments at different concentrations of distilled water in the reaction mixture. Methanol was added to the reaction mixture in one step on molar basis ratio of 1:3 between oil and methanol.

Abbreviations: Conv.—conversion; Cyc.—cycle; Wat.—water

Figure 17:
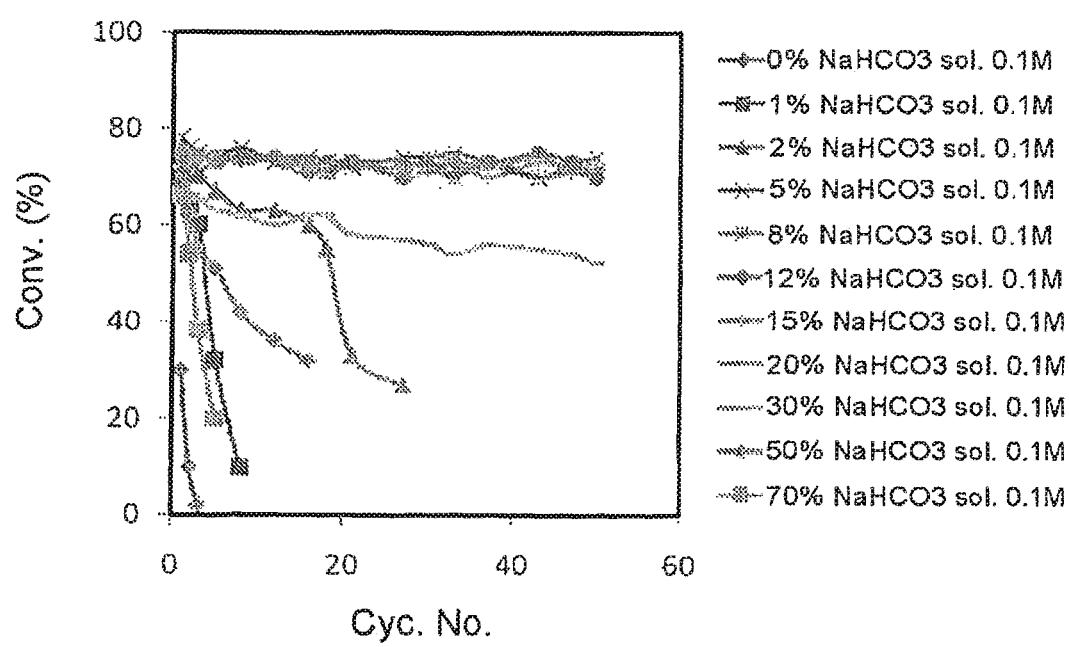

FIG. 17: The conversion of oleic acid to biodiesel and water after 6 hours of reaction using the same batch of biocatalyst (*Thermomyces lanuginosus* (TL) immobilized on a DVB-PS support) in multiple batch experiments at different concentrations of sodium bicarbonate solution of 0.1M Methanol was added to the reaction mixture in one step on molar basis ratio of 1:3 between oil and methanol.

Abbreviations: Conv.—conversion; Cyc.—cycle; Sol.—solution

Figure 18:
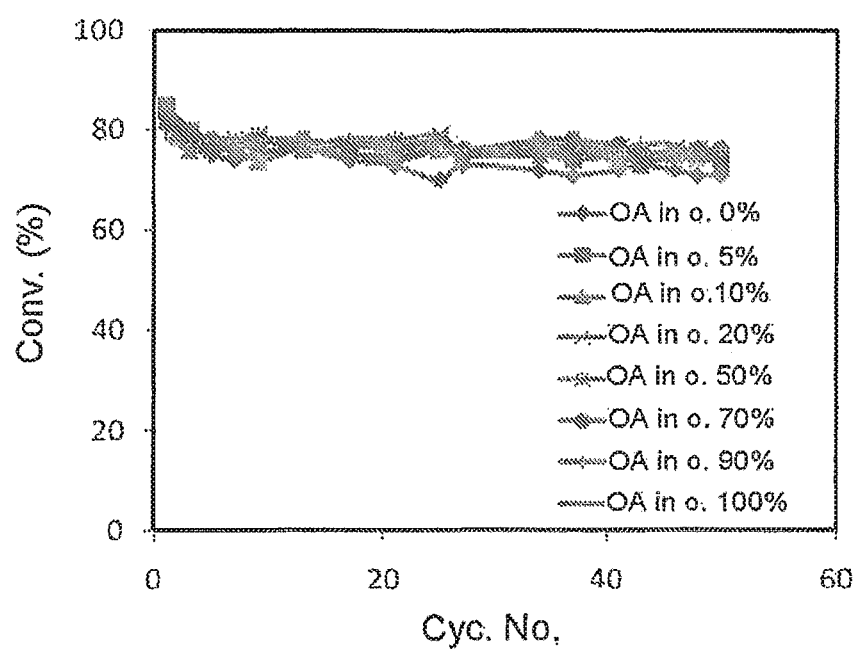
Figure 20:
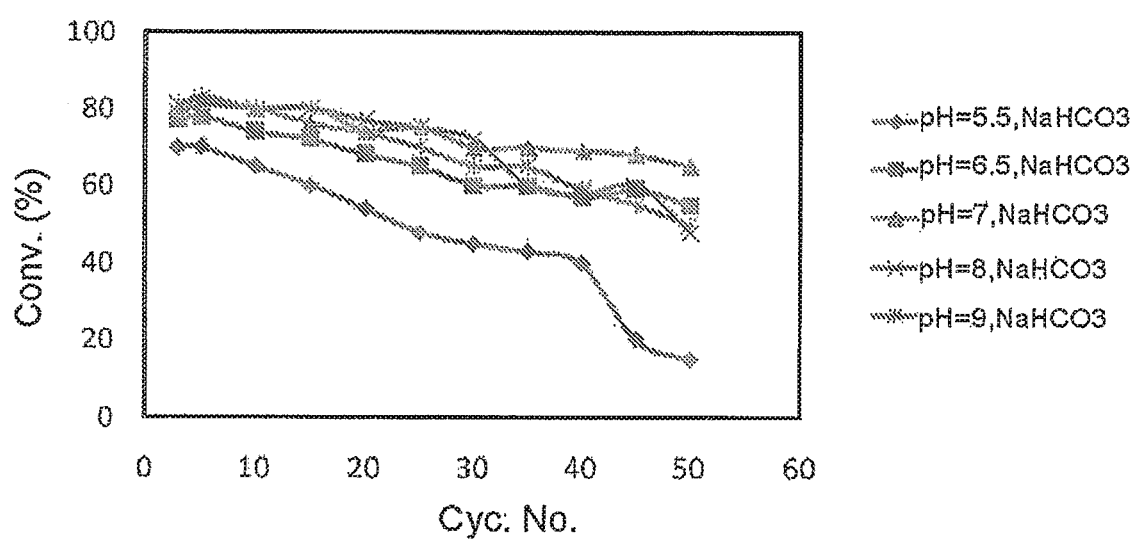

FIG. 18: The conversion of different mixtures of oleic acid and soybean oil triglycerides to biodiesel, glycerol and water after 6 hours of reaction using the same batch of biocatalyst (*Thermomyces lanuginosus* (TL) immobilized on a DVB-PS support) in multiple batch experiments in the presence of 8% wt. of sodium bicarbonate solution of 0.1M. Methanol was added to the reaction mixture in one step on molar basis ratio of 1:3 between oil and methanol.
Abbreviations: Conv.—conversion; Cyc.—cycle; Ol. Ac.—Oleic Acid FIG. 19: The conversion of crude oils containing phospholipids to biodiesel and glycerol after 6 hours of reaction using the same batch of biocatalyst (*Thermomyces lanuginosus* (TL) immobilized on a DVB-PS support) in multiple batch experiments in the presence of 8% wt. of sodium bicarbonate solution of 0.1M Methanol was added to the reaction mixture in one step on basis of molar ratio of 1:3 between oil and methanol.
Abbreviations: Conv.—conversion; Cyc.—cycle; RSBO—refined soybean oil; CSBO—Crude soybean oil; RSBO—refined soybean oil; PL—phospholipids; O.—oil;

FIG. 20: The conversion of soybean oil to biodiesel and glycerol after 6 hours of reaction using the same batch of (*Thermomyces lanuginosus* (TL) immobilized on a DVB-PS support) in multiple batch experiments at different pH values for sodium bicarbonate solution of 0.1M. The buffer concentration in the reaction medium was 8% wt. of the oil. Methanol was added to the reaction mixture in one step on basis of a molar ratio of 1:3 between oil and methanol.
Abbreviations: Conv.—conversion; Cyc.—cycle FIG. 21: The conversion of soybean oil to biodiesel and glycerol after 6 hours of reaction using the same batch of biocatalyst (*Thermomyces lanuginosus* (TL) immobilized on a DVB-PS support) in multiple batch experiments at different pH values for sodium acetate solution of 0.1M. The buffer concentration in the reaction medium was 8% wt. of oil. Methanol was added in to the reaction mixture in one step on basis of a molar ratio of 1:3 between oil and methanol.
Abbreviations: Conv.—conversion; Cyc.—cycle; Acet.—acetate FIG. 22: illustrates schematically a first embodiment of a system for the production of fatty acid alkyl esters according to an aspect of the invention.

Figure 23:
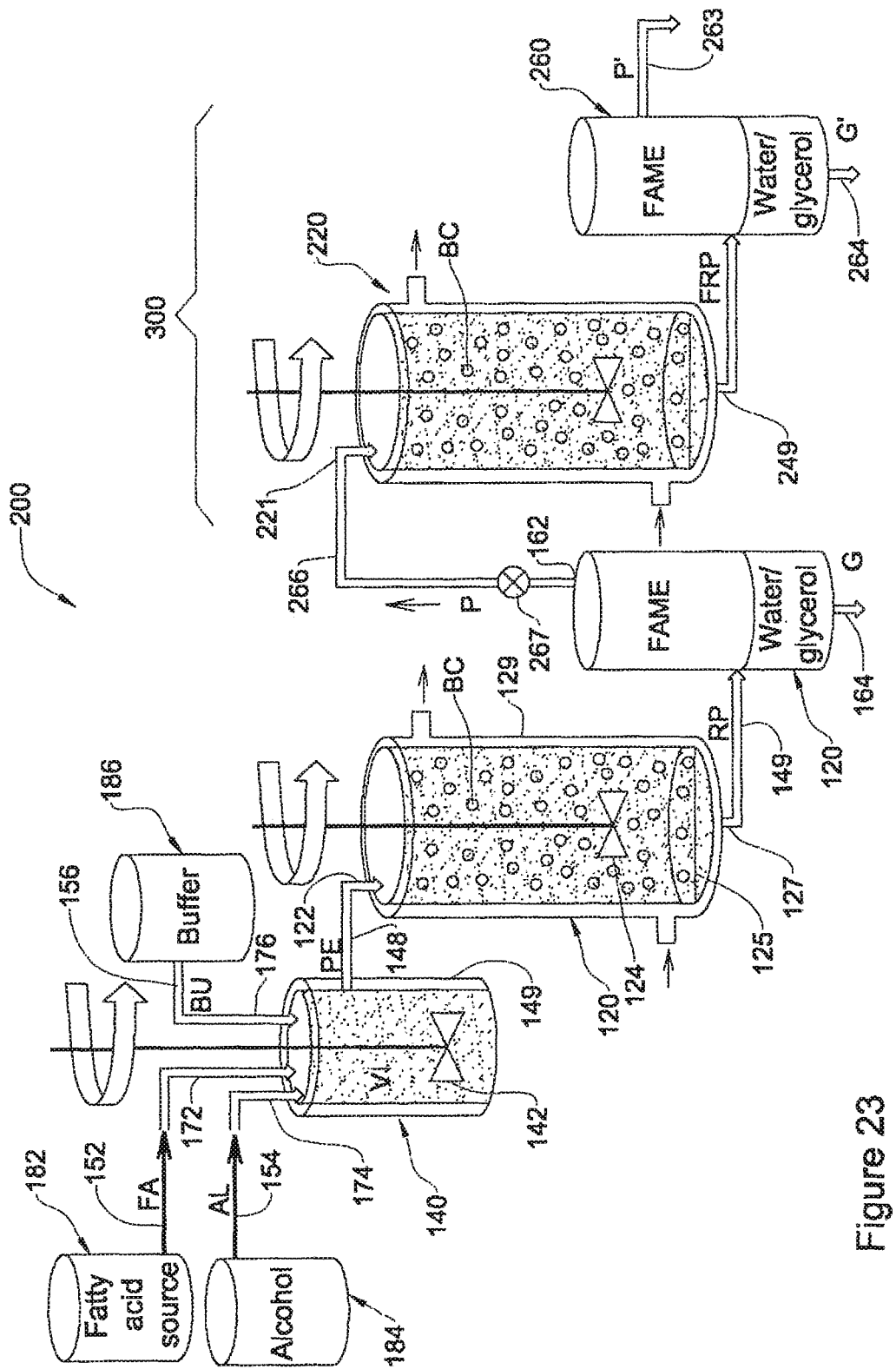

FIG. 23 illustrates schematically a second embodiment of a system for the production of fatty acid alkyl esters according to an aspect of the invention.

DETAILED DESCRIPTION OF THE INVENTION

In search for improvement of enzymatically catalyzed industrial processes, particularly processes for transesterification/esterification of a fatty acid source with an alcohol in the presence of immobilized lipase/s, the present inventors has developed specific conditions under which the stability of the immobilized lipase/s is preserved over scores of production cycles.

In an embodiment of the invention, the invention relates to a process for the preparation of alkyl esters of fatty acids, specifically short-chain alkyl esters of fatty acids, such as fatty acid methyl and ethyl esters (biodiesel) in a solvent-free alkaline microaqueous system. In specific embodiments, the alkaline microaqueous system is a mild alkaline microaqueous system. The process comprises providing a fatty acid source and reacting it with a free alcohol or an alcohol donor, in the presence of an immobilized lipase preparation, under said alkaline or mild alkaline conditions. Without being bound by theory, pretreatment of the fatty acid source with an alkaline buffer solution would result in neutralizing acids that might have an inhibitory effect on the enzyme. The quantity of alcohol required to complete the reaction up to 100% conversion may be added stepwise or in a one batch. Further, the alcohol may be short-chain alcohol, for example methanol or ethanol. Other alcohol donors may be used in the reaction with the fatty acid source in the presence of a hydrolase and allowing the reaction to proceed under suitable conditions, until said fatty acid source is converted to fatty acid alkyl esters, specifically, fatty acid methyl esters (FAME) or fatty acid ethyl esters, wherein said hydrolase preparation comprises one or more lipases, separately or jointly immobilized on a suitable macroreticular porous hydrophobic polymer-based support.

In an additional embodiment, the transesterification/esterification reaction between the fatty acid source and the alcohol or alcohol donor is carried out in an aqueous microenvironment, with the addition of water to the reaction mixture. In specific embodiments, water may be added at an amount higher than 0.0001% wt. (on basis of the fatty acid source). By water as used here is meant pure or distilled water, and also "water solutions" (also referred to as aqueous solutions), which may be, but are not limited to, tap water, sea water or water from any other natural water resource or reservoir, desalinated water, chemically or enzymatically purified or treated water, and any other aqueous solutions, for example dissolved salts solutions. The pH of the reaction system or of the water solution may vary, and may be, for example, about 3-11, for example 4-10, 5-10, 5-9, 6-10, 6-9, or 7-9.

The process of the invention may be carried out while continuously removing the formed glycerol and any excess water from the reaction mixture. The conversion of the fatty acid acyl groups or free fatty acids comprised in said fatty acid source to fatty acid alkyl, specifically methyl esters may be monitored at various time points during the reaction. The reaction medium may be removed by suitable means at any desired time point during the reaction, thereby stopping the reaction, and the formed fatty acid methyl esters and optionally the formed glycerol are isolated from the reaction medium. The reaction may be specifically stopped when the conversion of the fatty acid acyl groups or free fatty acids comprised in said fatty acid source to fatty acid methyl esters has reached at least 70%, for example at least 85%, or at least 90%.

The reaction system may be similar to that described in co-pending WO2009/069116. For example, the production system may use a stirred tank reactor with a bottom sintered glass or stainless steel filter which retains the biocatalyst in the reactor, however allows the reaction medium to permeate through out of the reactor. Such reactor configuration allows by-products, specifically glycerol and water, which are self-desorbed from the immobilized enzyme, to sink to the bottom of the reactor, and permeate out through the filter. The result is continuous removal of the desorbed formed glycerol and also of excess water, out of the reaction medium, leading to shift of the reacting towards synthesis, thereby reaching conversions above 98%. The biocatalyst used in this reactor may be comprised of a single or multi-types of lipases, in consideration of their positional specificity as well as their origin, as described herein. Alternative, two consecutive stirred tank reactors with a bottom filter may be used. A settling tank or centrifuge may be used between the two reactors. The first reactor may contain an immobilized biocatalyst comprised of a single or multi-types of lipases. The role of the settling tank or centrifuge between both reactors is to remove the formed glycerol and excess water from the reaction medium, leading to an increase in the conversion of the raw materials to their corresponding fatty acid alkyl esters to above 98% in the second reactor at reasonable reaction time. Some specific reaction systems and methods are described below.

The terms "reaction mixture", "reaction system" and "reaction medium" may be used herein synonymously.

The use of lipases immobilized on hydrophobic resins in the presence of alkaline buffer solution or water, as in embodiments of the process of the invention, ensures high stability of the enzyme and also avoidance of the accumulation of hydrophilic substances, such as water and the formed glycerol by-product, on the biocatalyst. In all aspects and embodiments of the process of the invention in which alkaline or mild alkaline buffer is used, it may be used in more than 0.001% alkaline or mild alkaline buffer solution, for example, but not limited to 0.01-5%, 0.05-5%, 0.1-5%, 0.5-5%, 0.01-50%, 0.05-50%, 0.1-50%, 0.5-50%, 1-50%, 1-45%, 1-40%, 1-35%, 1-30%, 1-25%, 1-20%, 1-15%, 1-10%, 1-8%, such as but not limited to more than 0.001%, 0.01%, 0.05%, 0.1%, 0.5%, 0.75%, 1%, 1.5%, 2%, 2.5%, 3%, 3.5%, 4%, 4.5%, 5%, 6%, 7%, 8%, 10%, 12%, 15%, 20%, 25%, 30%, 35%, 40%, 45%, 50%, 60%, or 70%. Levels of the alkaline or mild alkaline buffer solution may be up to 99% wt. In all aspects and embodiments of the invention where water or water solution are used, the water or water solution is used at levels of, but not limited to, more than 0.0001%, for example 0.0001-50%, 0.001-50%, 0.1-50%, 0.0001-30%, 0.001-30%, 0.1-30%, 0.0001-20%, 0.001-20%, 0.1-20%, such as but not limited to 0.001-5%, 0.01-5%, 0.05-5%, 0.1-5%, 0.5-5%, such as more than 0.0001%, 0.001%, 0.01%, 0.05%, 0.1%, 0.5%, 0.75%, 1%, 1.5%, 2%, 2.5%, 3%, 3.5%, 4%, 4.5%, 5%, 6%, 7%, 8%, 10%, 12%, 15%, 20%, 25%, 30%, 35%, 40%, 45%, 50%, or 70%. Water or water solution levels in the reaction mixture may be up to 99% wt. As mentioned, when alkaline solution is used, it may neutralize acids typically present in the fatty acid source or produced due to side reactions. Continuous active removal of these by-products may further increase the efficiency of the process. The isolated glycerol may be industrially used.

The fatty acid source used in the process of the invention may comprise at least one of soybean oil, canola oil, algae oil, rapeseed oil, olive oil, castor oil, palm oil, sunflower oil, peanut oil, cotton seed oil, Jatropha oil, crude corn oil, fish oil, animal-derived fat, waste cooking oil, brown grease, oil triglycerides derived from inedible plant sources, partial glycerides and free fatty acids derived from those oils or any mixture of at least two thereof, at any desired ratio.

Figure 19:
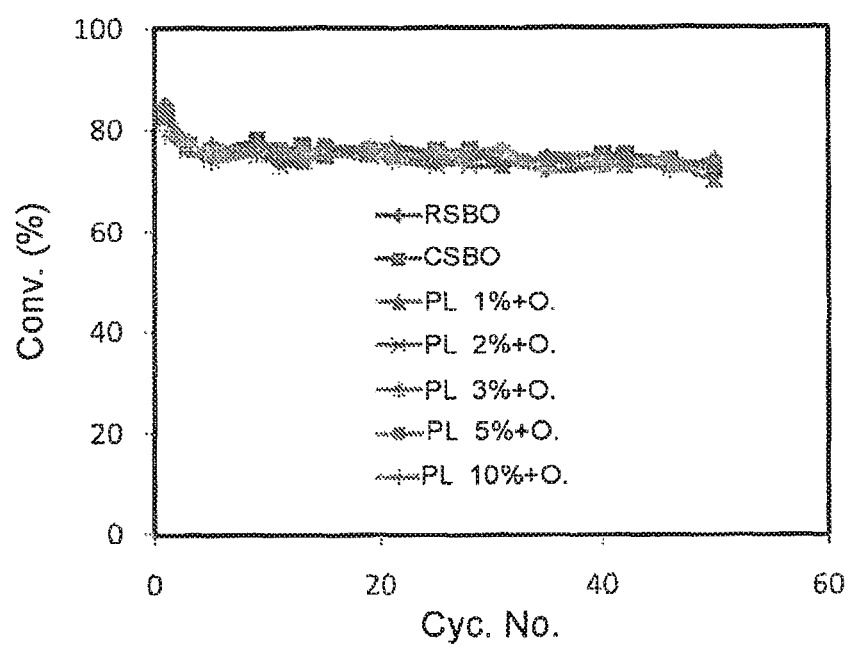

An example for the use of crude oil as the fatty acid source is presented in FIG. 19, where crude soybean oil was used. This figure also shows the use of oil containing phospholipids, at various concentrations, as the fatty acid source. The use of a mixture of free fatty acids with oil is illustrated, by way of example, in FIG. 18, where a mixture of oleic acid with oil, at various concentrations, and also of oleic acid per se (100%) served as the fatty acid source.

In all processes of the invention, the fatty acid short-chain alkyl esters formed by the reaction are specifically fatty acid methyl, ethyl, iso-propyl or butyl esters (biodiesel). Other medium-chain fatty alcohols ($C_6$-$C_{10}$) and long-chain fatty alcohols ($C_{12}$-$C_{22}$) might also be used in the process of production of this invention. These longer alcohols may be specifically suitable in the production of waxes, for example for cosmetic products.

The lipases may be lipases derived from *Thermomyces lanuginosus*, *Rhizomucor miehei*, *Mucor miehei*, *Pseudomonas* sp., *Rhizopus* sp., *Mucor javanicus*, *Penicillium roqueforti*, *Aspergillus niger*, *Chromobacterium viscosum*, *Acromobacter* sp., *Burkholderia* sp., *Candida antarctica* A, *Candida antarctica* B, *Candida rugosa*, *Alcaligenes* sp., *Penicillium camembertii*, papaya seeds and pancreatin, but are not limited thereto.

The lipases may be jointly immobilized on a suitable support, specifically a hydrophobic aliphatic polymer-based support or a hydrophobic aromatic polymeric support. Each of said lipases may be immobilized on a suitable support, wherein the supports on which the said lipases are immobilized are identical or different. Lipases employed may be regio-specific to their substrate, or random. When more than one lipase is used, the lipases may be immobilized on the same or on different hydrophobic supports. Lipases co-immobilized on the same support can exhibit identical or different substrate selectivities or regio-specificities to their substrates.

Lipases may be regio-specific (or site-specific), each used alone or in combination with lipases of same or different site specificity. When referring to positions sn-1, sn-2- or sn-3, these are positions on the glycerol backbone of the various glycerides. Thus, the lipases used in the process of the invention may possess selectivity towards sn-2 position higher than that of random lipases, i.e. their favour catalyzing the reaction between the alcohol or alcohol donor with the fatty acyl group of the sn-2 position, while random lipases exhibit the same transesterification activity for fatty acyl groups at all three positions on the glycerol backbone. Some lipases uniquely exhibit positional activity on sn-2 position, especially under specific conditions determined by the substrates, products, etc. Other lipases used in the process of the invention are sn-1,3 positional specific. They may be used alone or together with a random lipase, specifically lipase that has affinity to partial glycerides, and optionally a third lipase with a high affinity to the sn-2 position.

The support is specifically a porous and macroreticular hydrophobic support, which may be organic or inorganic. Examples of supports are porous inorganic supports, such as, but not limited hydrophobized silica- or and alumina-based supports, and hydrophobic organic supports such as, but not limited to polymeric or polymer-based support. The supports may optionally contain active functional groups selected from epoxy or and aldehyde groups, or ionic groups.

The insoluble support used in the processes of the invention is specifically a porous and reticular hydrophobic aliphatic or aromatic polymer-based support, such as Amberlite® XAD 1600 and Sepabeads® SP70 both comprised of porous microreticular resin prepared from divinylbenzene or from a mixture of divinylbenzene and polystyrene, Amberlite® XAD 7HP comprised of microreticular aliphatic acrylic polymer, and porous aliphatic polymer such as porous polypropylene (Accurel®).

The support may be a reticular hydrophobic polymer comprised of divinylbenzene, or a mixture of divinylbenzene and styrene, and reticular hydrophobic aliphatic polymer comprised of aliphatic acrylic polymers or polyalkene, such as polypropylene. Specific supports are porous matrices, of pore size in the range of 25-1000 Å, and more specifically in the range of 80-200 Å. The support also may be powderous or granular porous hydrophobic silica or other inorganic oxides. The support also may be powderous or granular porous hydrophobicized silica or other inorganic oxides. In specific embodiments, the surface area of the support resins is higher than 100 $m^2/g$.

The amount of the alkaline or mild alkaline aqueous solution to be supplemented into the lipase catalyzed transesterification/esterification reaction between the fatty acid source and the alcohol is generally adjusted in accordance with the other reaction conditions, starting materials, biocatalyst, etc. This amount can be varied, as recited and exemplified herein. This alkaline solution is prepared, for example, from an inorganic alkaline base or salt or from an organic base. Inorganic bases and salts are, for example, alkaline metal hydroxides, carbonates, bicarbonates, phosphates, sulfates, acetates and citrates. Organic bases can be, for example, primary, secondary or tertiary amines. Mixtures of these alkaline agents are also contemplated. In the process according to the invention, the pH of the microenvironment of the immobilized enzyme is maintained at alkaline or mild alkaline values. The addition of distilled water to the reaction system improves the performance of lipases immobilized on hydrophobic support (resins), as illustrated in FIGS. 4 and 5. As illustrated in FIG. 16, water may be added at even high quantities, while the stability of the biocatalyst (immobilized enzyme) is preserved, for example, at a water content of 30% wt., the same batch of biocatalyst exhibited 60% conversion activity after as many as 50 cycles. The addition of various alkaline buffers, with different pH values depending on the type of base used, also resulted in stabilization of lipases immobilized on hydrophobic supports (resins), as shown, for example, in FIGS. 2 and 3, and also in FIGS. 14, 15 and 17, which show that high levels of aqueous alkaline solutions did not harm the activity of the biocatalyst, with, for example, about 60% conversion rates, by the same batch of biocatalyst, at 30% wt. of 0.1M sodium bicarbonate solution in the reaction system, after more than as many as 50 cycles of the reaction. Without being bound by any theory, high concentrations of water are needed as the enzyme may preferably first hydrolyzes the ester bonds in the glyceride forms and consecutively esterify the formed free fatty acids with the supplemented alcohol. Added water also might suppress the extraction of water molecules essential to maintain the favored enzyme catalytic configuration. Carbonate and bicarbonate buffers are examples of mild bases that are efficient in increasing the stability of lipases immobilized on hydrophobic supports. Other suitable bases are described herein. Mild alkaline solution as used herein is generally a solution with a pH of from 7 to about 11, for example, 7-8.5, 7-9, 7-9.5, 7-10 or 7-11. Generally, the amount of alkaline or mild alkaline aqueous solution used is expressed by weight percents (wt. %) on basis of the amount of oil used in the reaction.

The use of lipases immobilized on porous hydrophobic polymer-based supports (resins) in the presence of an alkaline or mild alkaline solution, as well as in the presence of water or water solutions as defined herein, in the amounts recited above and also specifically exemplified, results in stabilizing the activity of the biocatalysts in the transesterification/esterification reactions between the fatty acid source and the alcohol. This is shown in the following Examples.

The fatty acid source is at least one of triglycerides, partial glycerides, free fatty acids, phospholipids, esters and amides of fatty acids or a mixture comprised of at least two said sources.

The production of fatty acid alkyl esters is carried out by transesterification or esterification, simultaneously or sequentially. Under such reaction system the biocatalyst activity is maintained with no significant activity losses in multiple uses and also avoids the accumulation of glycerol and water by-products or other hydrophilic compounds on the biocatalyst.

This invention provides processes employing specific immobilized interfacial enzymes that retain high activity and stability over many production cycles. Specifically, lipases and phospholipases preparation are used, in transesterification/esterification reactions. These reactions may be employed in the production of food articles, cosmetics and biofuels ("biodiesel"). Of particular interest, these enzymes may be used for the synthesis of fatty acids short-chain alkyl esters for use as "biodiesel".

The present invention employed stable immobilized interfacial enzymes, of high tolerance towards short-chain alcohols, such as methanol, ethanol and glycerol, as well as short-chain fatty acids, such as acetic acid. The use of these enzyme preparations also prevents accumulation on the immobilized biocatalyst of hydrophilic substances, in particularly glycerol and water.

In an embodiment of the invention there is provided a process for simultaneous or sequential transesterification/esterification reactions of a fatty acid source with an alcohol using one or more types of lipases, immobilized on a hydrophobic support (resin), in the presence of an alkaline or mild alkaline aqueous solution, for obtaining the desired product, namely, fatty acid alkyl esters, at near to complete conversions during reasonable reaction time, typically below 5 hours. A mild alkaline solution, for example a 0.001M, 0.1M, 0.5M or 1M solution of sodium bicarbonate, may be present in the reaction system in an amount of about 4% wt. or about 5% wt. or more than 5% wt. of the amount of oil used in the reaction, for example 6%, 8%, 10%, 12%, 15%, 20%, 25%, 30%, 40% or 50% wt.

As shown in the following Examples, the operational life time of lipases can also be extended by using hydrophobic resin support for lipase immobilization in combination with the use of an alkaline or mild alkaline buffer solution, at the various levels and ranges and sub-ranges of concentrations recited and exemplified herein, in the transesterification/esterification reaction medium. As further shown in the following Examples, the water content of the reaction mixture may be increased regardless of pH value. Thus, in another embodiment, the stability of the biocatalyst increases with increasing the water content of the reaction system by adding water, at the various levels and ranges and sub-ranges of concentrations recited and exemplified herein. The results show that the addition of an alkaline solution (FIGS. 2, 3, 14, 15, 17) or water (FIGS. 4, 5, 16) results in maintaining the enzyme activity and stability over many cycles of the reaction.

The alcohol or alcohol donor employed in the processes of the invention may be a short-chain alkyl alcohol, specifically C1-C6 alkyl alcohol, more specifically C1-C4 alkyl alcohol, and particularly methanol or ethanol or the alcohol donor may be mono-alkyl ester or dialkyl carbonate, such as dimethyl carbonate. An alcohol donor such as for example dialkyl carbonate can also serve as a source for alkalinity or mild alkalinity of the reaction system.

Figure 22:
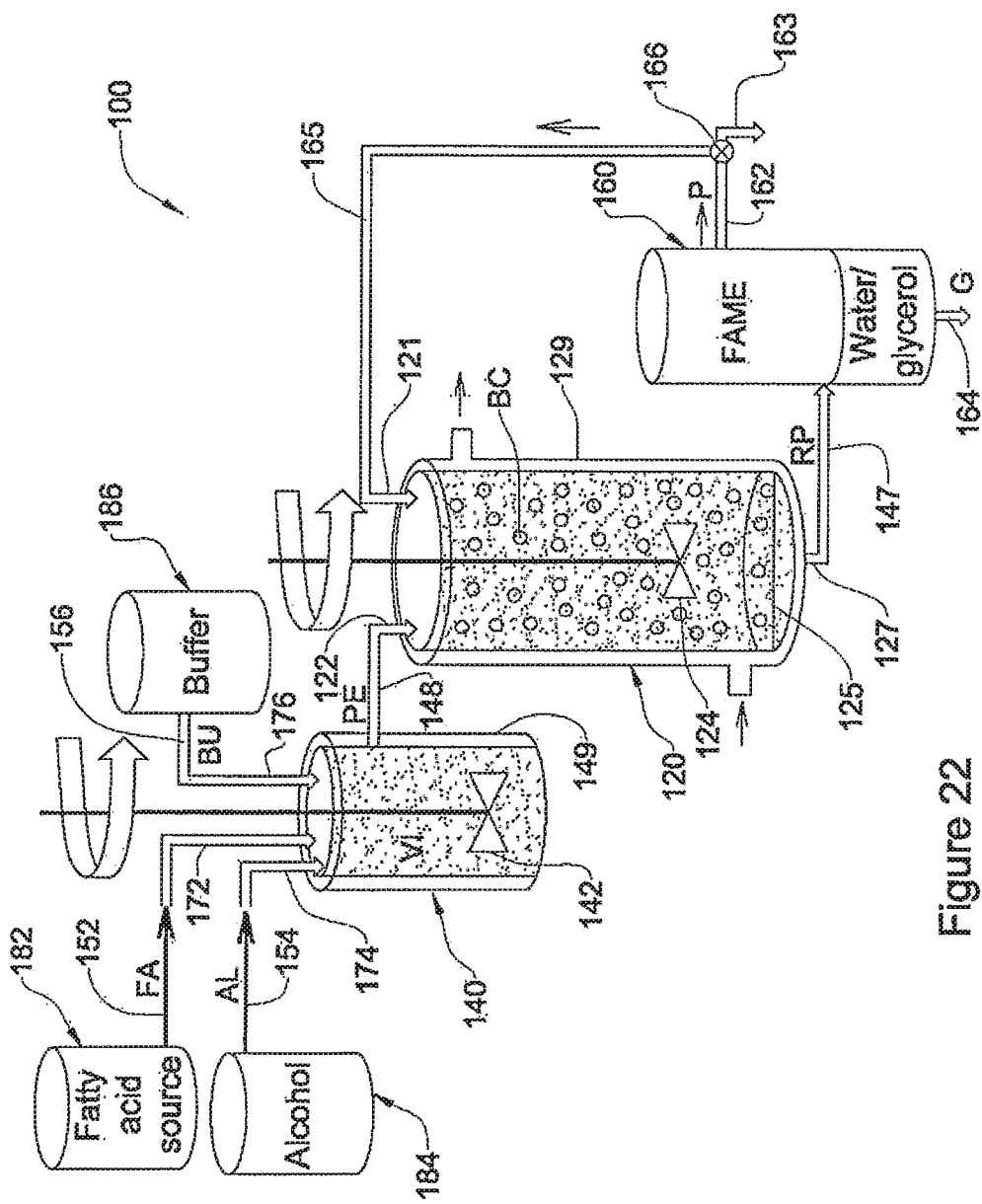

According to another aspect of the invention there is provided a system for the production of fatty acid alkyl esters. Referring to FIG. 22, a first embodiment of such a system, generally designated with the reference numeral 100, comprises a reactor vessel 120, a pre-reaction preparation vessel 140, and a product separation vessel 160.

Pre-reaction preparation vessel 140 is configured for receiving feedstock materials and buffer (and/or water), for forming a suitable emulsion therefrom, and for feeding the prepared emulsion PE (also referred to herein as emulsified feedstock) to the reactor vessel 120. In particular, such feedback materials may include fatty acid FA (for example waste cooking oil) from a fatty acid source 182, and alcohol AL (for example methanol) from alcohol source 184, and buffer (and/or water) BU from buffer/water source 186, provided via suitable supply lines 152, 154, 156, respectively, in fluid communication with said pre-reaction preparation vessel 140 via vessel inlets 172, 174, 176, respectively and suitable valves (not shown).

The pre-reaction preparation vessel 140 defines an internal volume V1 in which the reaction mixture, including feedstock materials and buffer/water, provided therein via vessel inlets 172, 174, 176, are mixed together by means of a suitable stirring system 142, driven by a powered source (not shown), to form emulsion PE. The pre-reaction preparation vessel 140 comprises an outer jacket 149 through which a suitable work fluid may be circulated to maintain the volume V1 at a desired steady state temperature. For example, the work fluid may be oil or water, heated or cooled in a different vessel (not shown) and pumped through the jacket 149 via suitable inlet and exit ports (not shown). In alternative variations of this embodiment, pre-reaction preparation vessel 140 may comprise a system of heating and/or cooling elements, for example electrically powered heating and/or cooling elements, instead of or in addition to the jacket 149.

Reactor vessel 120 is configured for receiving prepared emulsion PE from pre-reaction preparation vessel 140, for reacting the feedstock materials therein in the presence of a suitable biocatalyst BC to produce reaction products RP, and for feeding the reaction products RP from the reaction mixture to the product separation vessel 160. Outlet line 148 provides selective fluid communication between pre-reaction preparation vessel 140 and reactor vessel 120 via suitable valves (not shown) and allows the prepared emulsion PE prepared by the pre-reaction preparation vessel 140 to be fed to the reactor vessel 120 as desired.

The reactor vessel 120 defines an internal volume V2 in which the prepared emulsion PE in the reaction mixture, provided therein via vessel inlet 122, is reacted, and the reaction mixture may be stirred by means of a suitable stirring system 124, driven by a powered source (not shown) to form the reaction products RP. The biocatalyst BC may comprise a suitable enzyme and is provided in the form of immobilized enzyme beads which remain in the reactor vessel 120 until they become ineffective or are not sufficiently effective, whereupon they may be removed and replaced with new biocatalyst BC. For example, the biocatalyst BC may comprise lipase derived from *Thermomyces lanuginosus* immobilized on a hydrophobic and porous polystyrene-divinylbenzene-based resin.

The reactor vessel 120 comprises a thermal regulation system in the form of an outer jacket 129 through which a suitable work fluid may be circulated to maintain the volume V2 at a desired steady state temperature. For example, the work fluid may be oil or water, heated or cooled in a different vessel (not shown) and pumped through the jacket 129 via suitable inlet and exit ports 123. In alternative variations of this embodiment, the thermal regulation system comprises a system of heating and/or cooling elements, for example electrically powered heating and/or cooling elements, instead of or in addition to the jacket 129.

The lower part of the reactor vessel 120 comprises an outlet 127, and a suitable retaining arrangement in the form of filter 125 is provided upstream of the outlet 127 configured for, filtering the reaction mixture, in particular the reaction products RP prior to being removed from reactor vessel 120, and for preventing the biocatalyst BC from being removed with the reaction products RP.

The product separation vessel 160 is configured for separating out, from the reaction products RP, the desired product P (fatty acid alkyl ester), from by products including excess water and glycerol G. Outlet line 147 provides selective fluid communication between product separation vessel 160 and reactor vessel 120 via suitable valves (not shown) and allows the reaction products RP to be fed to the product separation vessel 160 from the reactor vessel 120 as desired. In this embodiment, the product separation vessel 160 comprises a centrifuge or gravity separation system for carrying out the aforesaid separation, and includes a first outlet 162 for outputting the product P, and a second outlet 164 for collecting the excess water and glycerol G. Product P may be collected via tap 163.

The system can thus be operated in a continuous production mode, in which prepared emulsion PE is fed into the reactor vessel 120, and the desired product P collected in a continuous manner via tap 163. The emulsion PE can be prepared and delivered in a continuous manner to the reactor vessel 120 to top up the volume of reactant therein at the same rate as the reaction products RP are being removed from outlet 127. Alternatively, emulsion PE can be prepared and delivered in batches to the reactor vessel 120 to top up the volume of reactant in the reaction mixture at discrete intervals whenever the level of reactants in the reactor vessel 120 drops to a particular minimum level following the continuous removal of reaction products RP via outlet 127. Of course, it is also possible to operate the system 100 to provide the desired product P in batches rather than continuously.

Alternatively, the system 100 may be operated in enhanced yield mode, wherein product P is, instead of being immediate collected via tap 163, re-routed to the reactor vessel 120 via an optional rerouting system, including line 165, vessel inlet 121 and valve 166, wherein valve 166 may be selectively operated to divert the product P from tap 163. When rerouted to reactor vessel 120, the product P may be further reacted therein with alcohol AL, provided via a separate line (not shown) from source 184, from a different alcohol source (not shown), or from source 184 via pre-reaction preparation vessel 140, to produce a higher yield of product P, which again may be separated out from byproducts using product separation vessel 160. When the alcohol is provided via preparation vessel 140, the latter is first emptied of the prepared emulsion PE, and suitable valves prevent fatty acids FA and optionally buffer/water being provided by respective sources 182 and 186.

Suitable pumps or gravity feeds and controllable valves may be provided for selectively transporting the respective materials through the respective lines 152, 154, 156, 148, 147, 165, and a suitable controller (not shown) monitors and controls operation of the system.

In at least some alternative variations of the first embodiment, the pre-reaction preparation vessel 140 may be integral with the reactor vessel 120. For example, the respective internal volumes V1 and V2 may be separated by a wall having an opening arrangement corresponding to the line 148. Alternatively, the respective internal volumes V1 and V2 may be contiguous, but internal volume V1 is sufficiently spaced from the biocatalyst BC to provide sufficient time for the emulsion PE to form before reaching the biocatalyst BC.

In alternative variations of the first embodiment, one, two or all of the fatty acid FA, alcohol AL, and buffer/water BU may be provided directly to the reactor vessel 120, bypassing the pre-reaction preparation vessel 140. For example, one or more of the fatty acid source 182, alcohol source 184, and buffer/water source 186, may be in selective fluid communication directly with reactor vessel 120 via suitable supply lines (not shown) bypassing the pre-reaction preparation vessel 140.

It is appreciated that all components of the system 100 according to the first embodiment, or alternative variations thereof, are of a suitable form and made from suitable materials as known in the art, such as to enable each component to carrying out the respective functions at the respective conditions, including temperature, pressure, pH and so on.

Referring to FIG. 23, a second embodiment of the system, designated with the reference number 200, comprises all the elements and features of the first embodiment, including alternative variations thereof, including all like-numbered components as in FIG. 22, mutatis mutandis, with some differences. For example system 200 also comprises: a reactor vessel 120, a pre-reaction preparation vessel 140, a product separation vessel 160, fatty acid source 182, alcohol source 184, buffer/water source 186, supply lines 152, 154, 156, vessel inlets 172, 174, 176, stirring system 142, outer jacket 149, outlet line 148 vessel inlet 122, stirring system 124, biocatalyst BC outer jacket 129, inlet and exit ports 123, outlet 127, filter 125, outlet line 147 first outlet 162 second outlet 164; as disclosed for the first embodiment, mutatis mutandis.

However, in the second embodiment, the line 165, tap 163 and valve 166 of the first embodiment are omitted, and instead an auxiliary reactor module 300 is operatively connected to the first outlet 162 of the product separation vessel 160.

Auxiliary reactor module 300 comprises an auxiliary reactor vessel 220 and an auxiliary product separation vessel 260, which in this embodiment are respectively substantially similar to reactor vessel 120 and product separation vessel 160, mutatis mutandis. In operation, the desired product P from product separation vessel 160 is routed to the auxiliary reactor vessel 220 via line 266, valve 267 and vessel inlet 221. When routed to auxiliary reactor vessel 220, the product P may be further reacted therein with alcohol AL, provided via a separate line (not shown) from source 184 or from a different alcohol source (not shown), to produce further reacted products FRP. Line 249 enables the further reacted products FRP to be transported to the auxiliary product separation vessel 260, which then operates to separate a higher yield of product P' from byproducts.

System 200 may be operated in a similar manner to system 100, mutatis mutandis.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention, will be limited only by the appended claims and equivalents thereof.

It must be noted that, as used in this specification and the appended claims, the singular forms "a", "an" and "the" include plural referents unless the content clearly dictates otherwise, Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

General

All experiments were carried out either in glass tubes of 30 ml in volume bottomed with a centered glass filter or in mechanically stirred reactors of 500 ml in volume bottomed with a sintered glass filter of porosity of 150-250 μm. Typical reaction medium contained fatty acid source, alcohol, normally, methanol or ethanol in molar basis 1:1 in relation to the fatty acid regardless free or bound on a glycerol backbone (for free fatty acids and monoglycerides 1:1, for diglycerides 1:2, and for triglycerides 1:3 in favor of the alcohol). The fatty acid source was premixed with different amounts of alkaline buffer, in specific embodiments sodium bicarbonate. The reactions were initiated by the addition of lipase immobilized on a hydrophobic resin (10-15% wt.) and the reaction medium was either shaken mechanically or stirred at 30° C. The alcohol amount was added equally in three steps each one hour apart, unless indicated differently. Reaction conversions were followed by taking samples from the reaction medium at different time intervals and analyzing fatty acid components. The conversion to biodiesel was calculated as: 100*peak area of fatty acid alkyl ester/sum of all peaks areas.

Lipase Immobilization:

Lipases were immobilized following standard procedures where lipase derived from a certain microorganism is solubilized in buffer solution of 0.1M at a certain pH value, for example 7.5. An organic or inorganic polymer resin was introduced into the lipase solution. The mixture was shaken at room temperature for 8 hour. Cold acetone was optionally added into the mixture in order to increase the protein enzyme precipitation on the resin. The mixture was filtered and the enzyme beads were dried to reduce the water content to less than 5%.

Different resins were used including hydrophobic polymer resins based on polystyrene/divinylbenzene, paraffin or any of their combinations, to obtain resins of hydrophobic characteristics. Typical hydrophobic resins used included Amberlite® XAD 1600 (Rohm & Haas, USA) and Sepabeads® SP70 (Resindion, Italy). Typical hydrophilic resins used included Duolite® D568 (Rohm & Haas) and porous silica gel. Lipases may be immobilized separately on a resin or different lipases are co-immobilized on the same resin.

Example 1

The transesterification activity of lipase derived from *Thermomyces lanuginosus* immobilized on Amberlite® XAD 1600 as a hydrophobic resin and on Duolite® D568 as a hydrophilic resin, and lipase derived from *Pseudomonas* sp. immobilized on Sepabeads® SP70 as a hydrophobic resin and on porous silica as a hydrophilic resin.

Reaction Conditions:

Refined and bleached soybean oil (20 g) containing 1% wt. of sodium bicarbonate solution of 0.1M. Methanol (2.5 ml) was added stepwise in three equivalent batches each one hour apart. The reaction medium containing 10% wt. lipase preparation was shaken at 300 rpm and 30° C. Results are shown in FIG. 1.

Figure 1:
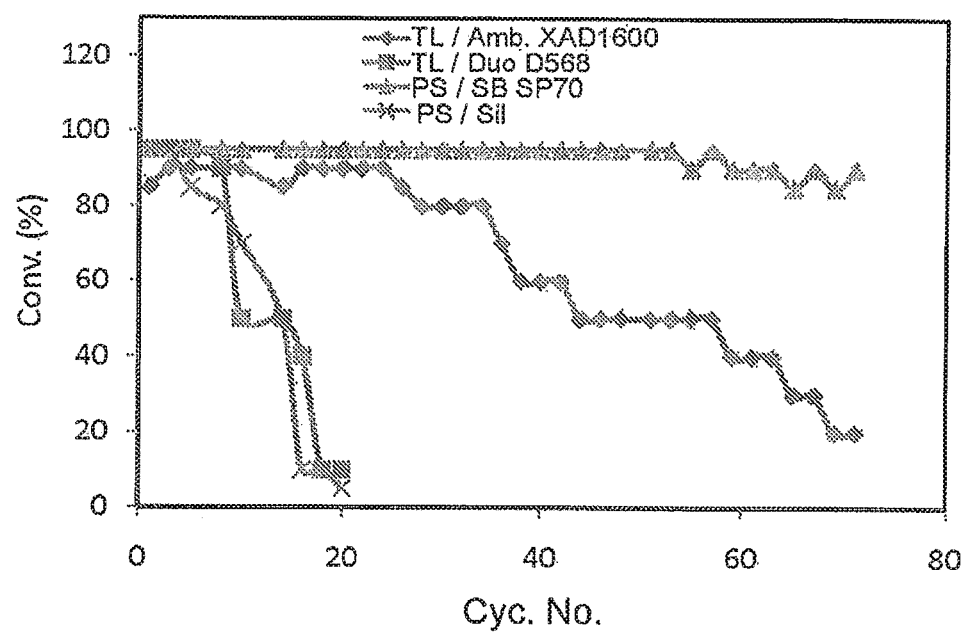
FIG. 1: The transesterification activity of lipase *Thermomyces lanuginosus* (TL) immobilized on Amberlite XAD 1600 (Amb. XAD 1600) as a hydrophobic resin and on Duolite D568 (Duo D568) as a hydrophilic resin, and lipase

The results presented in FIG. 1 show that both the *Thermomyces lanuginosus* and *Pseudomonas* sp. lipases immobilized on different resins in the presence of 1% wt. of sodium bicarbonate solution showed high transesterification activity during the first 5 cycles using the same batch of enzyme. It was observed that after the 5th batch, when the same batch of enzyme was used, the filtration of the reaction medium from the system became difficult due to the formation of gel-like deposit around the beads of both lipases immobilized on hydrophilic resins, namely Duolite® D568 and porous silica. The interesterification activity of both lipases immobilized on hydrophilic resins decreased sharply in further consecutive batches, and they became inactive after the 10th cycle. In contrast, *Pseudomonas* sp. lipase immobilized on the hydrophobic resin, Sepabeads® SP70, retained more than 80% of its initial activity after 70 cycles, while *Thermomyces lanuginosus* lipase immobilized on the hydrophobic resin, Amberlite® XAD1600, retained more than 20% of its initial activity after more than 70 cycles.

Example 2

A. The conversion of soybean oil to biodiesel and glycerol after 6 hours of reaction using the same batch of biocatalyst in multiple batch experiments.

Reaction Conditions:

Refined and bleached soybean oil (20 g) containing different concentrations of sodium bicarbonate solution of 0.1M. Methanol (2.5 ml) was added stepwise in three equivalent batches each one hour apart. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 2.

B. The conversion of soybean oil to biodiesel and glycerol after 6 hours of reaction using the same batch of biocatalyst in multiple batch experiments.

Reaction Conditions:

Refined and bleached soybean oil (20 g) containing different concentrations of sodium bicarbonate solution of 0.1M. Methanol (2.5 ml) was added stepwise in three equivalent batches each one hour apart. Lipase derived from *Pseudomonas* sp. immobilized on a hydrophobic and porous polystyrene-divinylbenzene-based resin, was used (10% wt.). The reaction medium was shaken at 300 rpm and 30° C. Results are shown in FIG. 3.

FIGS. 2 and 3 show that the amount of sodium carbonate in the reaction medium has a major role on the operational life of *Thermomyces lanuginosus* and *Pseudomonas* sp. lipases immobilized on hydrophobic resins. It can be seen in FIGS. 2 and 3 that in the absence of an alkaline solution both immobilized lipases drastically lose their activity after a few cycles, while the same immobilized lipases maintain their transesterification activity over multiple uses in the presence of sodium bicarbonate solution as a base in the reaction system. The results for both immobilized enzymes show that increasing the amount of sodium bicarbonate solution in the reaction medium in the range of 0-4% wt. results in decreasing the loss of enzyme activity in multiple uses of the same batch of immobilized enzyme.

Example 3

A. The conversion of soybean oil to biodiesel and glycerol after 6 hours of reaction using the same batch of biocatalyst in multiple batch experiments.

Reaction Conditions:

Refined and bleached soybean oil (20 g) containing different concentrations of distilled water. Methanol (2.5 ml) was added stepwise in three equivalent batches each one hour apart. Lipase derived from *Thermomyces lanuginosus* immobilized on a hydrophobic and porous polystyrene-divinylbenzene-based resin was used (10% wt.). The reaction medium was shaken at 300 rpm and 30° C. Results are shown in FIG. 4.

B. The conversion of soybean oil to biodiesel and glycerol after 6 hours of reaction using the same batch of biocatalyst in multiple batch experiments.

Reaction Conditions:

Refined and bleached soybean oil (20 g) containing different concentrations of distilled water. Methanol (2.5 ml) was added stepwise in three equivalent batches each one hour apart. Lipase derived from *Pseudomonas* sp. immobilized on a hydrophobic and porous polystyrene-divinylbenzene-based resin, was used (10% wt.). The reaction medium was shaken at 300 rpm. and 30° C. Results are shown in FIG. 5.

FIGS. 4 and 5 show that the transesterification activity using the same batch of lipases *Thermomyces lanuginosus* and *Pseudomonas* sp. immobilized on hydrophobic resins in multiple experiments is also affected by the amount of water in the reaction system. It can be seen that increasing the water amount from none (zero) to 4% wt. resulted in maintaining higher residual transesterification activity of biocatalyst when used in consecutive cycles. The results presented in FIGS. 2 to 5 evidently show that using mild base, such as sodium bicarbonate solution in the transesterification reactions is favored for maintaining the activity of lipases immobilized on hydrophobic resins when used in consecutive cycles.

Example 4

The conversion of a mixture of free fatty acids (FFA's) and soybean oil to biodiesel, and glycerol and water by-products after 4 hours of esterification/transesterification using the same batch of biocatalyst in multiple batch experiments.

Reaction Conditions:

A mixture of free fatty acids soybean hydrolysate (50% wt.) and soybean oil (50% wt.) of initial FFA value 72 mg KOH/1 g containing different amount of sodium bicarbonate solution of 0.1M. Methanol (4.5 ml) was added stepwise in three equivalent batches each one hour apart. Lipase derived from *Pseudomonas* sp. immobilized on a hydrophobic and porous polystyrene-divinylbenzene-based resin, was used (20% wt.). The reaction medium was shaken at 300 rpm and 30° C. Results are shown in FIG. 6.

FIG. 6 shows that different amount of base solution has a major effect on the simultaneous esterification reaction of FFA present in the reaction mixture comprised of equivalent proportions of soybean oil hydrolysate and soybean oil triglycerides. It can be seen that *Pseudomonas* sp. lipase immobilized on a hydrophobic resin lost its esterification activity when no alkaline solution was added into the esterification/transesterification reaction system, while the same biocatalyst has maintained its activity in consecutive cycles when 1 and 2% wt. of sodium bicarbonate solutions of 0.1 M were added separately into the reaction systems. The results presented in FIG. 6 show that the use of *Pseudomonas* sp. lipase immobilized on a hydrophobic resin reduced the FFA content in the presence of 1% and 2% wt. of sodium bicarbonate solution of 0.1M from initial value of 72 mg KOH/1 g down to 8 and 6 mg KOH/1 g in average, respectively, and maintained this activity in 22 subsequent cycles.

Example 5

The esterification of soybean oil hydrolysate to biodiesel and water after 4 hours of reaction using the same batch of biocatalyst in multiple batch experiments.

Reaction conditions: Free fatty acids soybean hydrolysate (20 g) of FFA value of 150 mg KOH/1 g containing 1% wt. sodium bicarbonate solution of 0.1M. Methanol (2 ml) was added into the reaction medium in one batch. Lipase derived from *Pseudomonas* sp. immobilized on a hydrophobic and porous polystyrene-divinylbenzene-based resin, was used (10% wt.). The reaction medium was shaken at 300 rpm and 30° C. Results are shown in FIG. 7.

FIG. 7 shows that *Pseudomonas* sp. lipase immobilized on a hydrophobic resin is also capable of catalyzing the esterification of free fatty acids to form fatty acid methyl esters and water by-product. The results show that the lipase preparation maintained its esterification/transesterification activity in a medium containing 1% sodium bicarbonate solution of 0.1M over more than 25 cycles using the same batch of biocatalyst without the observation of any significant loss of activity.

Example 6

The transesterification of fish oil with ethanol after 6 hours of reaction using the same batch of biocatalyst in multiple batch experiments.

Reaction Conditions:

Refined fish oil (20 g) containing 1% sodium bicarbonate solution of 0.1 M. Ethanol (2.5 ml) was added stepwise in three equivalent batches each one hour apart. Lipases derived from *Thermomyces lanuginosus* and *Pseudomonas* sp. immobilized on Amberlite® XAD 1600, were used separately (10% wt.). The reaction medium was shaken at 300 rpm and 30° C. Results are shown in FIG. 8.

FIG. 8 shows that both lipases derived from *Thermomyces lanuginosus* and *Pseudomonas* sp. immobilized on hydrophobic resins are also capable of catalyzing the transesterification of fish oil triglycerides with ethanol to form fatty acid ethyl esters and glycerol by-product. The results also show that both biocatalyst preparations maintained their transesterification activity in the presence of 1% sodium bicarbonate solution without significant activity losses over more than 20 cycles using the same batch of biocatalyst.

Example 7

The transesterification of Tallow fat with ethanol after 6 hours of reaction using the same batch of biocatalyst in multiple batch experiments.

Reaction Conditions:

Tallow fat (16 g) containing fatty acid ethyl ester of tallow fat (4 g) and 1% potassium carbonate solution of 1M. Ethanol (2.5 ml) was added stepwise in three equivalent batches each one hour apart. Lipases derived from *Thermomyces lanuginosus*, *Pseudomonas* sp. immobilized on Amberlite® XAD 1600 (10% wt.) were used separately or in combination at an equivalent ratio. The reaction medium was shaken at 300 rpm and 37° C. Results are shown in FIG. 9.

FIG. 9 shows that both lipases derived from *Thermomyces lanuginosus* and *Pseudomonas* sp. separately or in combination immobilized on hydrophobic resins are also capable of catalyzing the transesterification of tallow fat triglycerides with ethanol to form fatty acid ethyl esters and glycerol by-product. The feedstock of the reaction medium was comprised of tallow fat (80%) and fatty acid ethyl esters derived from tallow fat in order to lower the melting point of the reaction medium. The results presented in FIG. 9 show that all biocatalysts retained more than 80% of their initial activity in the presence of mild alkaline solution, such as potassium carbonate of 1M, when the same batch of biocatalysts were used in 100 consecutive cycles.

Example 8

The treatment of the transesterification/esterification reaction medium obtained after 4 hours containing FFA value of 7 mg KOH/1 g using *Pseudomonas* sp. lipase or *Thermomyces lanuginosus* lipase immobilized on hydrophobic porous resins with *Candida Antarctica* B lipase immobilized on a hydrophobic porous resin and methanol (ratio of 1:10 on molar basic between FFA and methanol, respectively) using the same batch of biocatalyst (10% wt.) in multiple batch experiments. The reaction medium was shaken at 300 rpm and 30° C. Results are shown in FIG. 10.

FIG. 10 shows that the transesterification reaction medium obtained after treatment either with *Thermomyces lanuginosus* lipase or *Pseudomonas* sp. lipase as described above, which typically contain FFAs values of 3-7 mg KOH/1 g, can be treated with *Candida antarctica* B lipase immobilized on either hydrophilic or hydrophobic support, results in reducing the FFA value down to less than 2 mg KOH/1 g. The immobilized lipase can maintain its activity in more than 100 cycles.

Example 9

The transesterification/esterification activity of lipases derived from *Alcaligenes* sp. (AL), *Pseudomonas* sp. (PS) and *Thermomyces lanuginosus* (TL) immobilized on DVB-PS as a hydrophobic resin and on Duolite® D568 as a hydrophilic ion exchange resin, and granulated porous silica as hydrophilic enzyme adsorbent.

Reaction Conditions:

Refined and bleached soybean oil (20 g) containing 2% wt. of sodium bicarbonate solution of 0.1M. Methanol (2.5 ml) was added stepwise in three equivalent batches each one hour apart, unless stated, otherwise added in one step. The reaction medium containing 10% wt lipase preparation was shaken at 300 rpm and 30° C. Results are shown in FIGS. 10-13.

The results presented in FIGS. 10-13 show that when *Alcaligenes* sp., *Pseudomonas* sp. and *Thermomyces lanuginosus* lipases were immobilized on hydrophilic resins high conversions were obtained during the first few cycles however the enzyme activity dropped sharply to reach low conversions after 10 cycles using the same bath of biocatalyst. It was also observed that after the fifth batch, when the same batch of enzyme was used, the filtration of the reaction medium from the system became difficult due to the formation of gel-like deposit around the beads of both lipases immobilized on hydrophilic resins, namely weak ion exchange resin and porous silica.

In contrast, *Alcaligenes* sp., *Pseudomonas* sp. and *Thermomyces lanuginosus* lipases immobilized on DVB-PS hydrophobic resins, all retained more than 80% of their initial activity after 50 cycles. FIGS. 10-13 show that all lipases showed high activity in the first batch and slightly decreased after the second batch most probably due to wash out of any loosely bound enzyme on the resin.

Example 10

A. The conversion of soybean oil to biodiesel and glycerol after 6 hours of reaction using the same batch of biocatalyst in multiple batch experiments.
Reaction Conditions:
Refined and bleached soybean oil (20 g) containing different concentrations of sodium bicarbonate solution of 0.1M. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 14.
B. The conversion of soybean oil to biodiesel and glycerol after 6 hours of reaction using the same batch of biocatalyst in multiple batch experiments.
Reaction Conditions:
Refined and bleached soybean oil (20 g) containing different concentrations of sodium bicarbonate solution of 0.1M. Methanol (2.5 ml) was added in one step. Lipase derived from *Pseudomonas* sp. immobilized on a hydrophobic and porous polystyrene-divinylbenzene-based resin, was used (10% wt.). The reaction medium was shaken at 300 rpm and 30° C. Results are shown in FIG. 15.
FIGS. 14 and 15 show that the amount of sodium bicarbonate in the reaction medium has a major role on the operational life of lipases *Thermomyces lanuginosus* and *Pseudomonas* sp. immobilized on hydrophobic resins. It can be seen in FIGS. 4 and 5 that in the absence of a mild alkaline solution both immobilized lipases drastically lost their activity after a few cycles, while the same immobilized lipases maintained their transesterification activity over multiple uses in the presence of sodium bicarbonate solution as a base in the reaction system. The results for both immobilized enzymes show that increasing the amount of sodium bicarbonate solution in the reaction medium in the range of 0-30% wt. results in increased enzyme transesterification activity in multiple uses of the same batch of immobilized enzyme. Increasing the amount of sodium bicarbonate solution to more than 30% wt. led to decreasing the enzyme activity. Without being bound by theory, this decrease may probably be attributed to washing out of the enzyme from the resin.

Example 11

The conversion of soybean oil to biodiesel and glycerol after 6 hours of reaction using the same batch of biocatalyst in multiple batch experiments.
Reaction Conditions:
Refined and bleached soybean oil (20 g) containing different concentrations of distilled water. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 16.
FIG. 16 shows that the amount of water in the reaction medium also has a major role on the operational life of *Thermomyces lanuginosus* lipase immobilized on hydrophobic resins. It can be seen in FIG. 16 that in the absence of water the immobilized lipase drastically loses its activity after a few cycles, while the same immobilized lipase maintains its transesterification activity over multiple uses in the presence of water in the reaction system. The results for the immobilized enzyme show that increasing the amount of water in the reaction medium in the range of 0-30% wt. results in increased enzyme transesterification activity in multiple uses of the same batch of immobilized enzyme, while increasing the amount of water above 30% wt. led to decreasing the enzyme activity.

Example 12

The conversion of oleic acid to biodiesel and water after 6 hours of reaction using the same batch of biocatalyst in multiple batch experiments.
Reaction Conditions:
Oleic acid (20 g) containing different concentrations of sodium bicarbonate solution of 0.1M. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 17.
FIG. 17 shows that the concentration of sodium bicarbonate solution in the reaction medium has major role in determining the esterification activity of *Thermomyces lanuginosus* immobilized on a hydrophobic and porous polystyrene-divinylbenzene-based resin. It can be seen in FIG. 17 that in the absence of water in the reaction system the lipase immobilized on hydrophobic resin lost its activity sharply when used in multiple batch experiments. Increasing the concentration of sodium bicarbonate solution in the range of 0-20% wt. resulted in increasing the esterification activity of the biocatalyst in multiple uses. Increasing the aqueous phase amount above 30% wt resulted in loss of enzyme activity in multiple uses, most likely due to wash out of the enzyme from the resin.

Example 13

The conversion of mixtures of oleic acid and soybean oil triglycerides to biodiesel, glycerol and water after 6 hours of reaction using the same batch of biocatalyst in multiple batch experiments.
Reaction Conditions:
Refined and bleached soybean oil containing different concentrations of oleic acid (20 g) was supplemented with 8% wt. of sodium bicarbonate solution of 0.1M. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 18.
FIG. 18 show that *Thermomyces lanuginosus* lipase immobilized on a hydrophobic and porous lipase resin and in the presence of buffer solution is capable to esterify and transesterify free fatty acids, and glycerides to form biodiesel and by-products glycerol and water. The results also show that the immobilized lipases maintain their catalytic activity with no significant activity losses in multiple uses of the same batch of biocatalyst for 50 cycles.

Example 14

The conversion of crude oils containing phospholipids to biodiesel and glycerol after 6 hours of reaction using the same batch of biocatalyst in multiple batch experiments.

Reaction Conditions:

Crude soybean oil containing different concentrations of phospholipids (20 g) was supplemented with 8% wt, of sodium bicarbonate solution of 0.1M. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 19.

FIG. 19 shows the transesterification activity of *Thermomyces lanuginosus* lipase immobilized on a hydrophobic and porous divinylbenzene-polystyrene resin. Analysis results show in contrast to previous literature reports that lipases immobilized on hydrophobic resins in the presence of sodium bicarbonate solution are capable of transesterifying of glycerides including phospholipids to yield biodiesel, and the by-products glycerol and glycerophospholipids. Also, the results show that lipases maintain their transesterification catalytic activity when the same batch of immobilized enzyme is used in multiple uses.

Example 15

The conversion of soybean oil to biodiesel and glycerol using the same batch of biocatalyst (*Thermomyces lanuginosus* (TL) immobilized on a DVB-PS support) in multiple batch experiments at different pH values for sodium bicarbonate solution of 0.1M.

Reaction Conditions:

Refined and bleached soybean oil (20 g) containing 8% wt of sodium bicarbonate solution of 0.1M at different pH values. Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 20.

The conversion of soybean oil to biodiesel and glycerol using the same batch of biocatalyst (*Thermomyces lanuginosus* (TL) immobilized on a DVB-PS support) in multiple batch experiments at different pH values for sodium acetate solution of 0.1M.

Reaction conditions: Refined and bleached soybean oil (20 g) containing 8% wt of sodium acetate solution of 0.1M at different pH values Methanol (2.5 ml) was added in one step. Lipase derived from *Thermomyces lanuginosus* immobilized on a hydrophobic and porous polystyrene-divinylbenzene-based resin, was used (10% wt.). The reaction medium was shaken at 300 rpm and 30° C. Results are shown in FIG. 21.

The results presented in FIG. 20 show that at pH values of above 5.5 the biocatalyst has retained more than 60% of its initial transesterification activity after 50 cycles using the same batch of enzyme. The results show clearly that there was linear decrease in enzyme activity at pH value of 5.5 and the enzyme activity reached below 20% of the initial enzyme activity.

Figure 21:
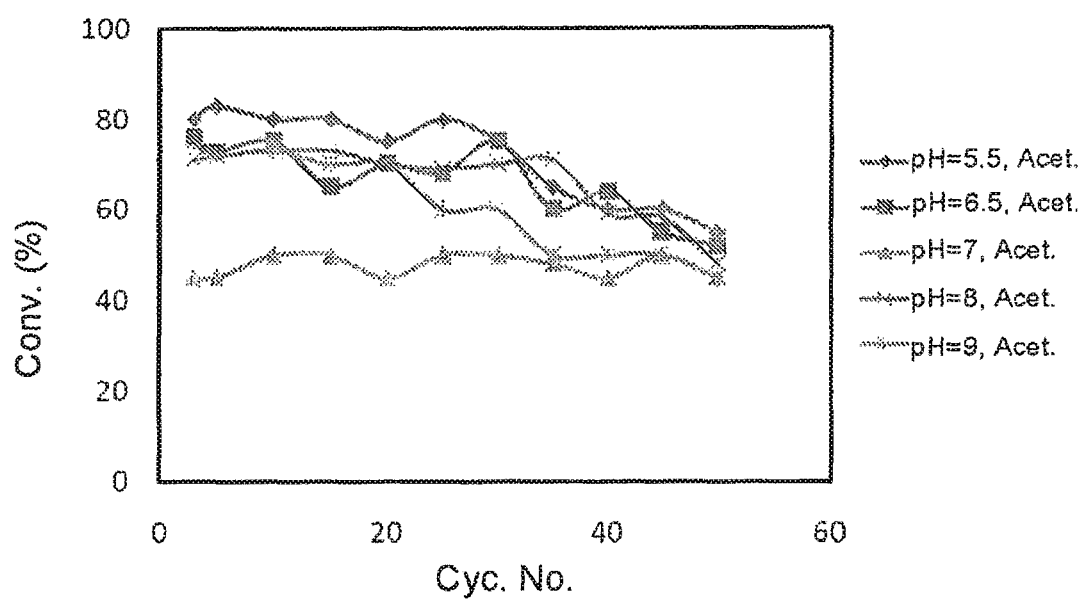

Similar trend has been observed when buffer acetate was used at pH values of above 6.5 where the enzyme has retained more than 50% of its initial activity after 50 repeated use (FIG. 21). The results presented in FIG. 21 show also that when sodium acetate solution of pH 5.5 was used the enzyme activity was low however maintained constant after 50 cycles of repeated use.

Example 16

Transesterification/esterification of waste-cooking oil containing 10% FFA with methanol to form biodiesel, water and glycerol using the first embodiment of the system illustrated in FIG. 22.

Reaction Conditions:

Waste-cooking oil (1100 g) containing 2% of sodium bicarbonate solution of 0.1M and methanol (140 g) were first premixed in pre-reaction preparation vessel 140 to form an emulsion, which was then introduced to the reactor vessel 120 having an internal volume V2 of about 2 liters. The reaction mixture was mixed in the reactor vessel 120 with a lipase derived from *Thermomyces lanuginosus* immobilized on a hydrophobic and porous polystyrene-divinylbenzene-based resin (30% wt of the oil) for 6 hours at 30° C. The reaction mixture was filtered off through the filter 125 and fed to product separation vessel 160. Glycerol and excess of water were removed from the reaction mixture in the product separation vessel 160. The upper phase containing of the fatty acid methyl esters and the unreacted glycerides were re-introduced to the reactor vessel 120 via rerouting line 165, and stirring in the reactor vessel 120 was resumed after the addition of methanol (110 g) in to the reaction medium in the reactor vessel 120. The conversion to methyl ester after 2 hours was 98%. An emulsified reaction medium (prepared emulsion) containing waste-cooking oil (83% wt), methanol (15%) and sodium bicarbonate solution of 0.1M (2%) was continuously fed into the reactor vessel 120 at a flow rate of about 30 ml/min. The conversion to fatty acid methyl esters was maintained to more than 3 months without significant activity losses when using the same batch of biocatalyst derived from *Thermomyces lanuginosus* lipase immobilized on a macroporous hydrophobic resin.

The invention claimed is:

1. A process for simultaneous and/or sequential enzymatic transesterification and esterification of a fatty acid source with a $C_{1-6}$ alkyl alcohol, to form fatty acid $C_{1-6}$ alkyl esters, the process comprising the steps of:
   (1) providing a fatty acid source in a reaction vessel, wherein said fatty acid source comprises mono-, di- or tri-glycerides and their mixtures at any ratio, in the absence or presence of free fatty acids or their derivatives;
   (2) adding to said fatty acid source provided in step (1) water, in an amount of at least 2% wt. of the fatty acid source, to give a mixture of said fatty acid source and water;
   (3) adding to said mixture of fatty acid source and water obtained in step (2) an immobilized lipase preparation, wherein the immobilized lipase preparation comprises at least one lipase immobilized on a hydrophobic porous polymeric support selected from the group consisting of a hydrophobic aliphatic polymer-based support, a hydrophobic acrylic polymer-based support, a hydrophobic aromatic polymer-based support;
   (4) stepwise adding to the mixture obtained in step (3) a $C_{1-6}$ alkyl alcohol or alcohol donor whilst mixing to give a reaction medium comprising said fatty acid source, immobilized enzyme, water and $C_{1-6}$ alkyl alcohol, wherein the reaction medium has a pH from about 4 to about 10;
   (5) allowing the reaction between said fatty acid source and said alcohol or alcohol donor to proceed in said vessel under stirring and/or shaking until conversion of the fatty acid acyl groups or free fatty acids comprised in said fatty acid source to fatty acid $C_{1-6}$ alkyl esters has reached at least 70%, to give fatty acid $C_{1-6}$ alkyl esters, glycerol and, respectively, water;
   (6) filtering off the reaction medium; and
   (7) separating the filtered reaction medium obtained in step (6) by phase separation and collecting an upper phase comprising fatty acid $C_{1-6}$ alkyl esters product and any unreacted residual fatty acid source,
wherein said immobilized lipase preparation retains at least 80% of its activity for at least 20 production cycles.

2. The process of claim 1, wherein said water is added to the said reaction vessel in an amount of from 2% wt. to 30% wt. of the fatty acid source.

3. The process of claim 1, wherein said alcohol donor is a mono-alkyl ester or a di-alkyl carbonate, or mixture thereof.

4. The process of claim 1, wherein said fatty acid derivatives are phospholipids, wax esters or sterol esters.

5. The process of claim 1, wherein said at least one lipase is a lipase derived from any one of *Rhizomucor miehei*, *Pseudomonas* sp., *Rhizopus niveus*, *Mucor javanicus*, *Rhizopus oryzae*, *Aspergillus niger*, *Penicillium camembertii*, *Alcaligenes* sp., *Acromobacter* sp., *Burkholderia* sp., *Thermomyces lanuginosus*, *Chromobacterium viscosum*, *Candida antarctica* B, *Candida rugosa*, *Candida antarctica* A, *papaya* seeds and pancreatin.

6. The process of claim 1, wherein said immobilized lipase is capable of separately, simultaneously, or sequentially catalyzing esterification of free fatty acids to yield fatty acid alkyl esters and water, and transesterification of triglycerides and partial glycerides to yield fatty acid alkyl esters and glycerol.

7. The process of claim 1, wherein said immobilized lipase preparation comprises at least two lipases which may be each separately immobilized on a hydrophobic support or said at least two lipases are co-immobilized on the same hydrophobic support, wherein said lipases each possess identical or different regio-specificity.

8. The process of claim 7, wherein said lipases are capable of separately, simultaneously or consecutively catalyzing esterification of free fatty acids to yield fatty acid alkyl esters and water, and transesterification of triglycerides and partial glycerides to yield fatty acid alkyl esters and glycerol.

9. The process of claim 1, wherein said fatty acid source is any one of plant oil, animal fat, algal oil, fish oil, waste oil and any mixtures thereof.

10. The process of claim 1, wherein said alcohol is methanol and said fatty acid $C_{1-6}$ alkyl esters are fatty acid methyl esters (FAME Biodiesel).

11. The process of claim 1, wherein said transesterification and esterification are carried out in stirred-tank reactors or in packed-bed column reactors operating in batch or continuous modes.

12. The process of claim 1, wherein the water is any one of tap water, sea water or water from any other natural water resource or reservoir, desalinated water, chemically or enzymatically purified or treated water.

* * * * *